(12) United States Patent
Haberer et al.

(10) Patent No.: US 12,295,949 B2
(45) Date of Patent: May 13, 2025

(54) TREATMENT OF THE GASTROINTESTINAL TRACT WITH DIMERIC NAPHTHALIMIDE COMPOUNDS

(71) Applicant: Alumend, LLC, Sioux Falls, SD (US)

(72) Inventors: Barbara R. Haberer, Hartford, SD (US); Ronald E. Utecht, Madison, SD (US)

(73) Assignee: Alumend, LLC, Sioux Falls, SD (US)

( * ) Notice: Subject to any disclaimer, the term of this patent is extended or adjusted under 35 U.S.C. 154(b) by 58 days.

(21) Appl. No.: 17/986,350

(22) Filed: Nov. 14, 2022

(65) Prior Publication Data

US 2024/0050425 A1 Feb. 15, 2024

Related U.S. Application Data

(60) Provisional application No. 63/395,854, filed on Aug. 7, 2022.

(51) Int. Cl.
*A61K 31/473* (2006.01)
*A61K 41/00* (2020.01)
*A61P 1/04* (2006.01)

(52) U.S. Cl.
CPC ........ *A61K 31/473* (2013.01); *A61K 41/0057* (2013.01); *A61P 1/04* (2018.01)

(58) Field of Classification Search
CPC .................................................. A61K 31/473
See application file for complete search history.

(56) References Cited

U.S. PATENT DOCUMENTS

| | | |
|---|---|---|
| 5,235,045 A | 8/1993 | Lewis et al. |
| 5,565,551 A | 10/1996 | Lewis et al. |
| 5,766,600 A | 6/1998 | Lewis et al. |
| 5,917,045 A | 6/1999 | Lewis et al. |
| 6,410,505 B1 | 6/2002 | Lewis et al. |
| 7,514,399 B2 | 4/2009 | Utecht et al. |
| 10,053,521 B2 | 8/2018 | Utecht et al. |
| 10,851,185 B2 | 12/2020 | Utecht et al. |
| 10,959,995 B2 | 3/2021 | Haberer et al. |
| 2019/0255300 A1 | 8/2019 | Cottone et al. |
| 2019/0255330 A1 | 8/2019 | Sabesan |
| 2020/0016377 A1 | 1/2020 | Kaufman et al. |
| 2020/0139020 A1 | 5/2020 | Antoni et al. |
| 2020/0179659 A1 | 6/2020 | Kaufman et al. |

OTHER PUBLICATIONS

Donnan et al., EndoFLIP in the Esophagus: Assessing Sphincter Function, Wall Stiffness, and Motility to Guide Treatment; Science Direct, vol. 49, Issue 3, Sep. 2020, pp. 427-435; https://doi.org/10.1016/j.gtc.2020.04.002.

Cook, Clinical disorders of the upper esophageal sphincter; GI Motility online, May 16, 2006; doi:10.1038/gimo37 (28 pgs).

Blount et al., Fluoroscopically Guided Balloon Dilation of the Esophagus; Semin Intervent Radiol. Jun. 2010; 27(2):232-240. doi: 10.1055/s-0030-1253519.

Hwang et al., Esophageal stricture induced by an ultraslim upper endoscope in a novel rabbit model of corrosive injury; Scand J Gastroenterol. Jan. 2014;49(1):30-4. doi: 10.3109/00365521.2013. 848229. Epub Oct. 28, 2013. (Abstract provided).

Paterson et al., Esophageal motility disorders; GI Motility online (2006) doi:10.1038/gimo20; Published May 16, 2006.

*Primary Examiner* — Paul V Ward
(74) *Attorney, Agent, or Firm* — ArentFox Schiff LLP; Bruce D. Jobse

(57) ABSTRACT

Disclosed are methods for treating stenosis in the digestive system and conditions associated with irregular esophageal tone with dimeric naphthalimide compounds and their pharmaceutically acceptable salts. Also disclosed are methods for enhancing recovery following esophageal surgery that entail treatment of the surgical area with dimeric naphthalimide compounds and their pharmaceutical salts.

52 Claims, 19 Drawing Sheets
(19 of 19 Drawing Sheet(s) Filed in Color)

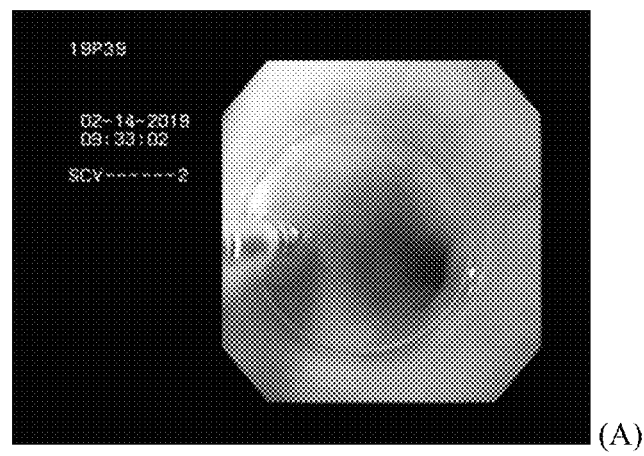
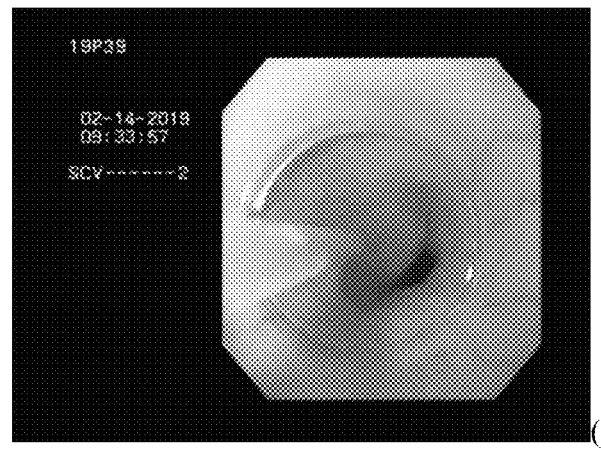
Figs. 2A and B

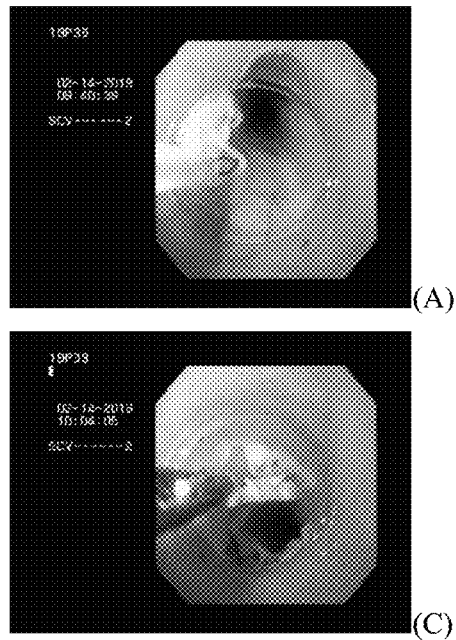
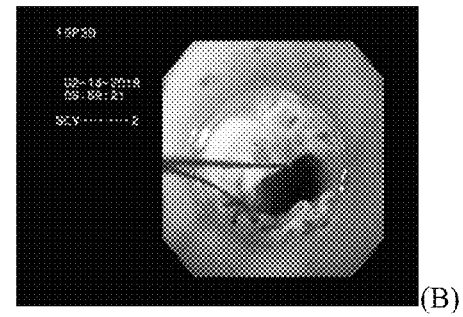
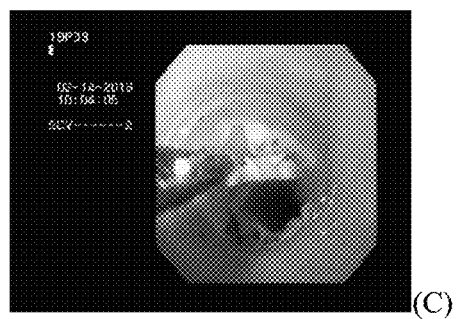
Figs. 3A-C
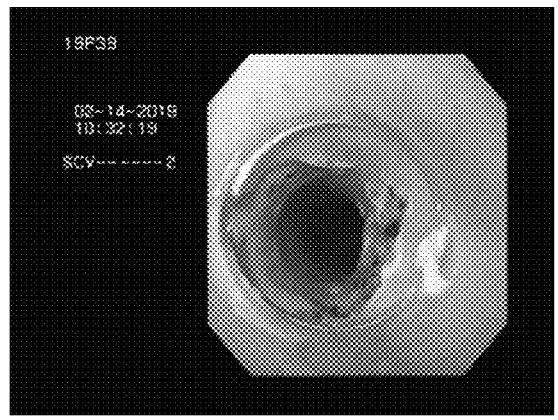
Fig. 4

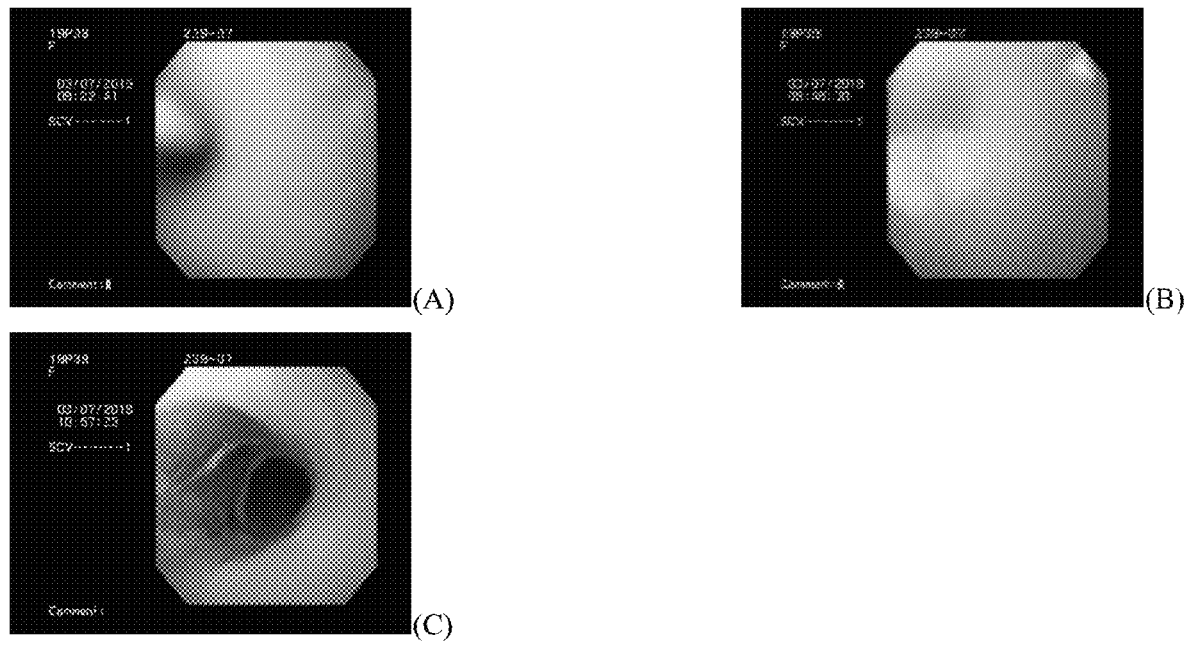
Figs. 8A-C
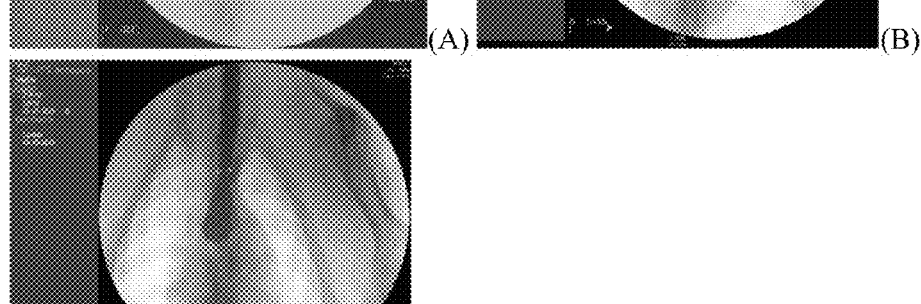
Figs. 9A-C

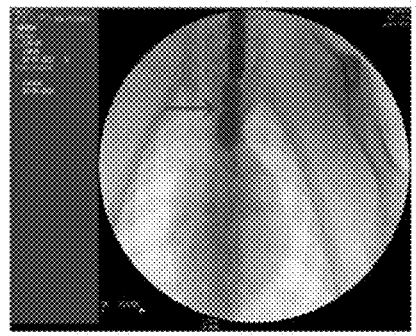
(A)
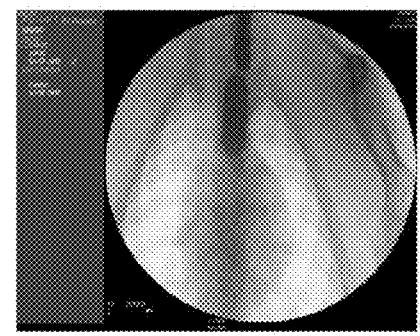<br/>(B)
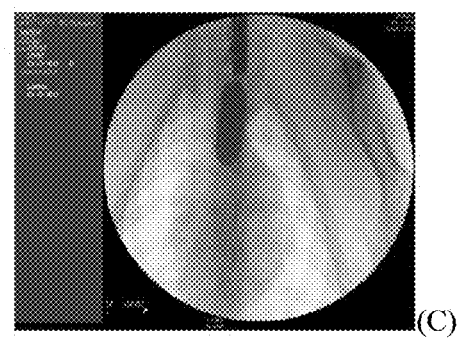(C)
Figs. 10A-C
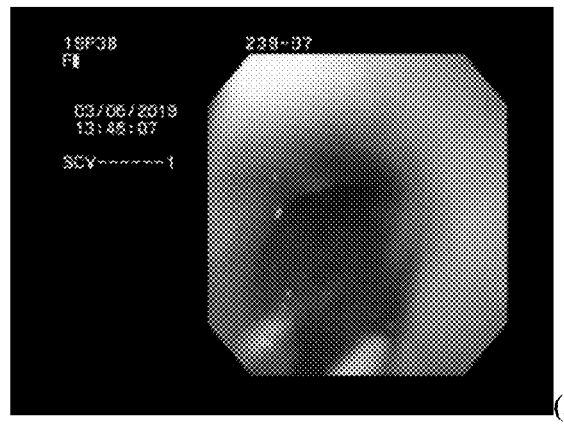(A)
(B)
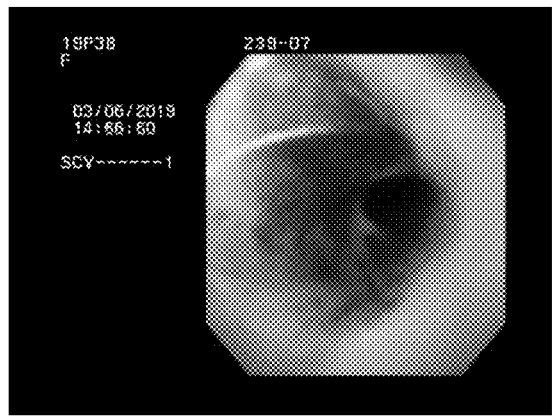
Figs. 11A-B

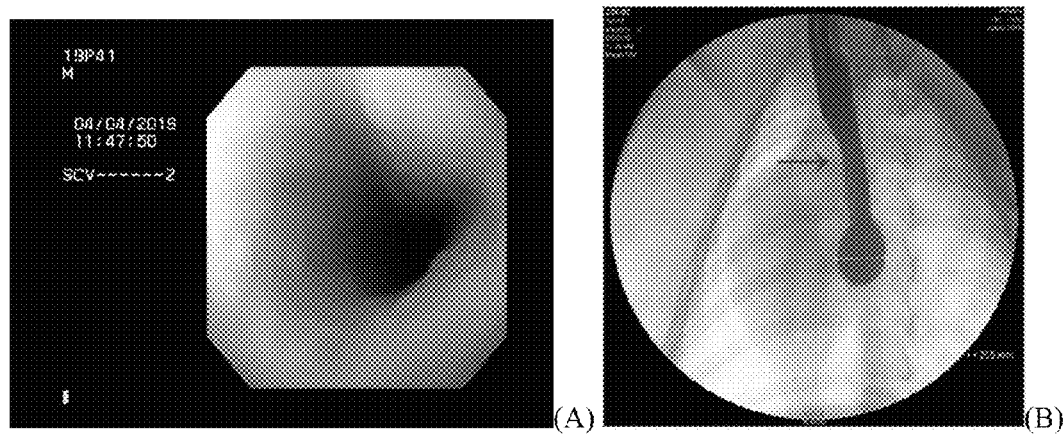
Figs. 12A-B
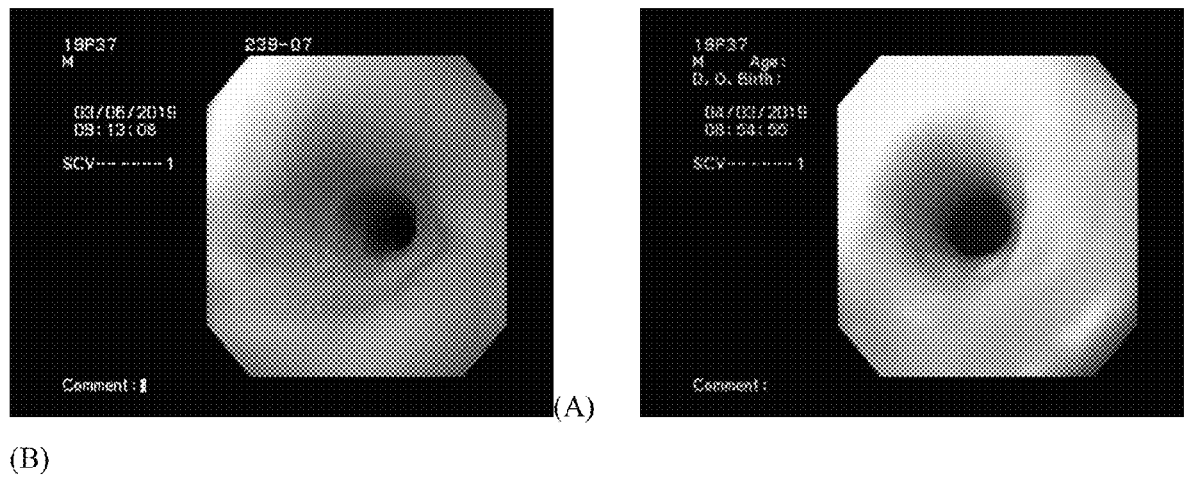
Figs. 13A-B
Fig. 14

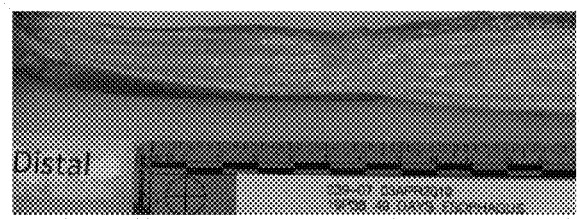
Fig. 18
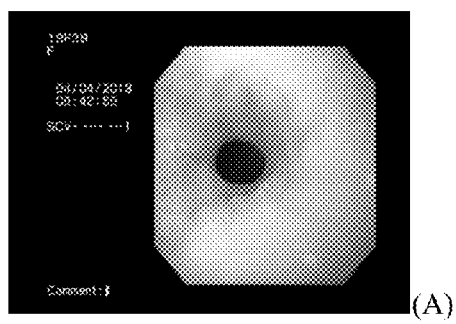
(A)
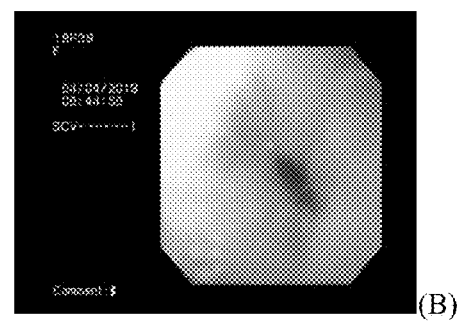
(B)
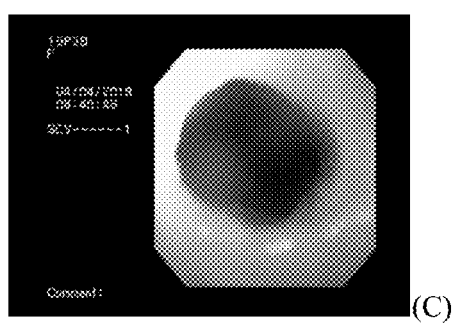
(C)
Figs. 19A-C
Fig. 20

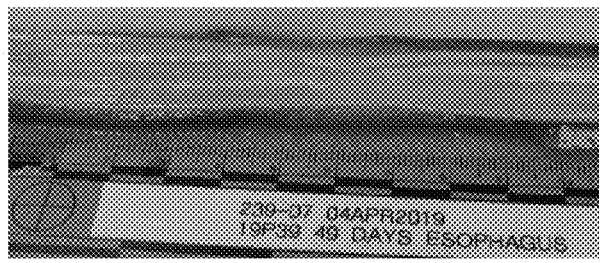
Fig. 21
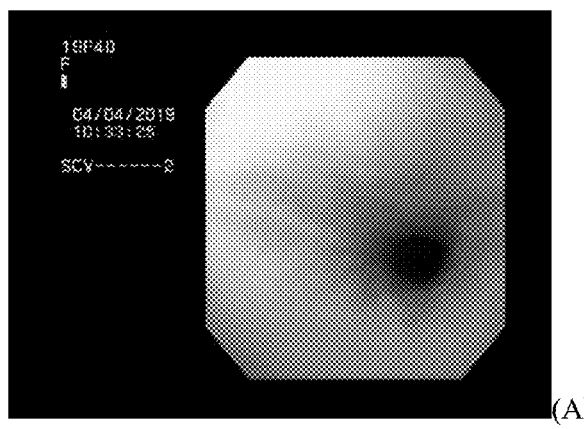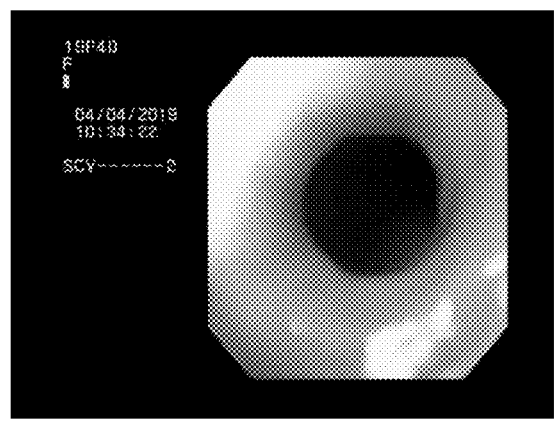
(A)
(B)
Figs. 22A-B
Fig. 23

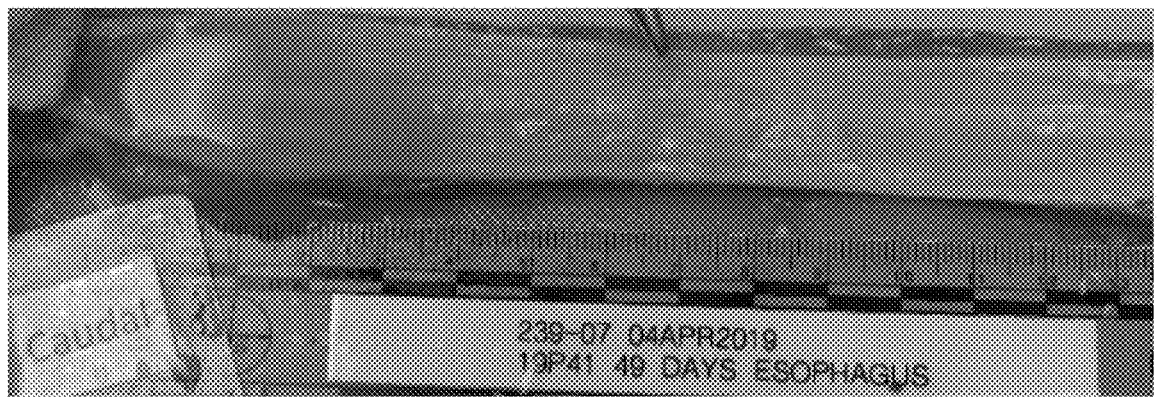
Fig. 27
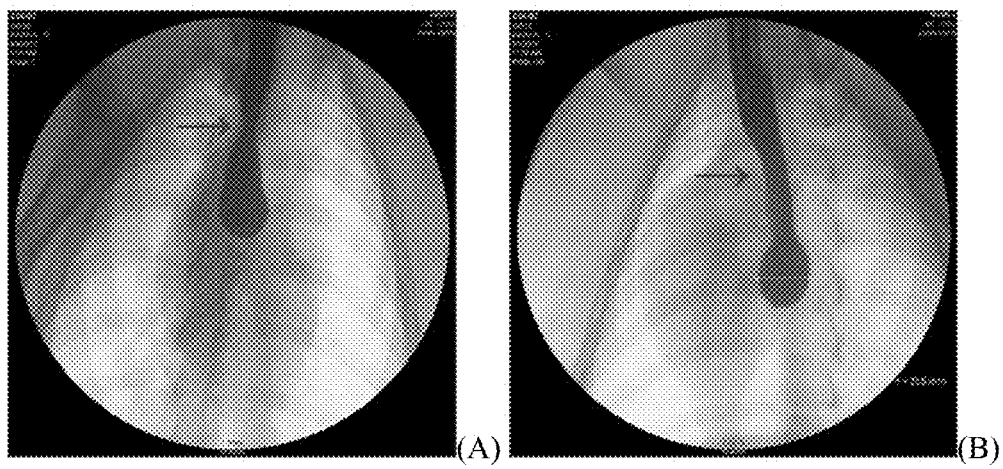
Figs. 28A-B
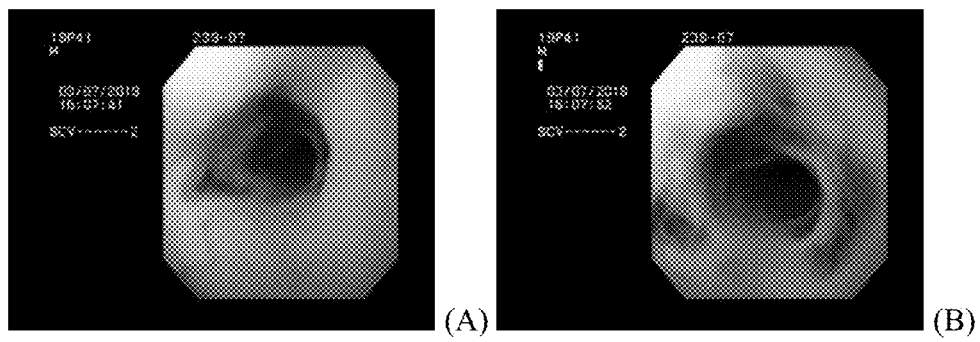
Figs. 29A and B

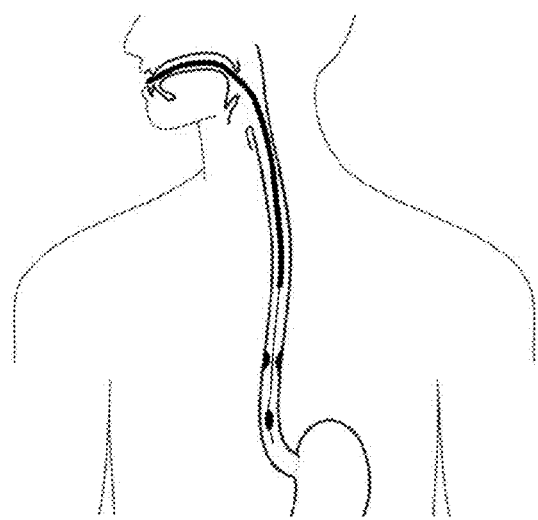 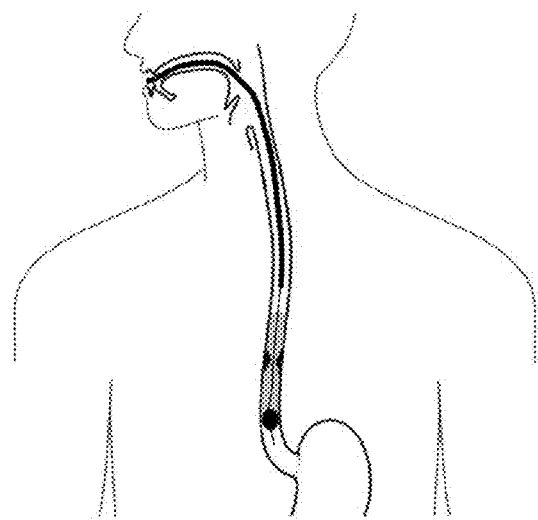
Fig. 30A
Fig. 30B

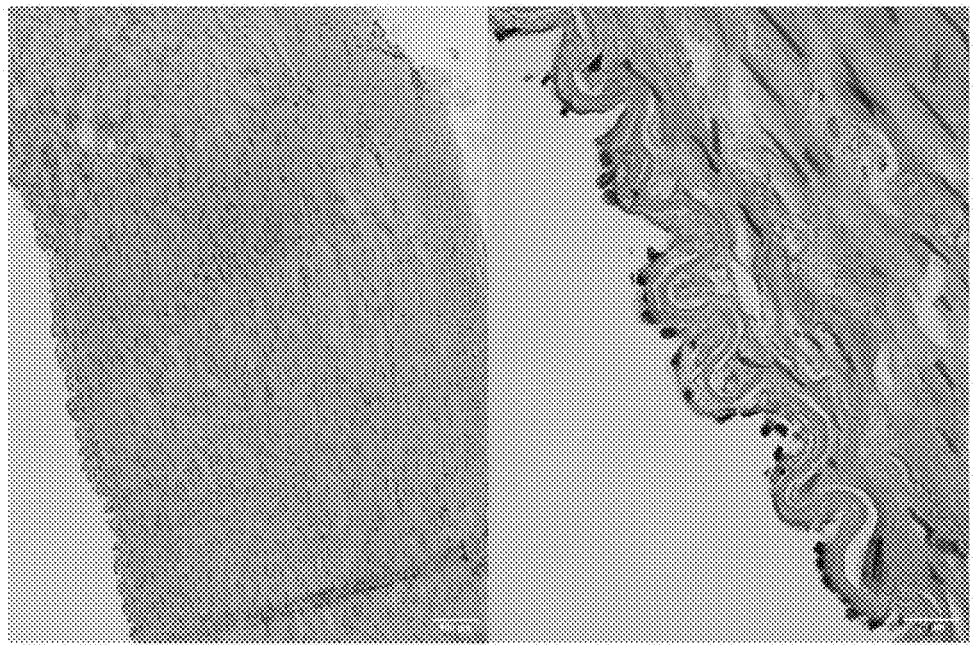
Fig. 31A                                    Fig. 31B
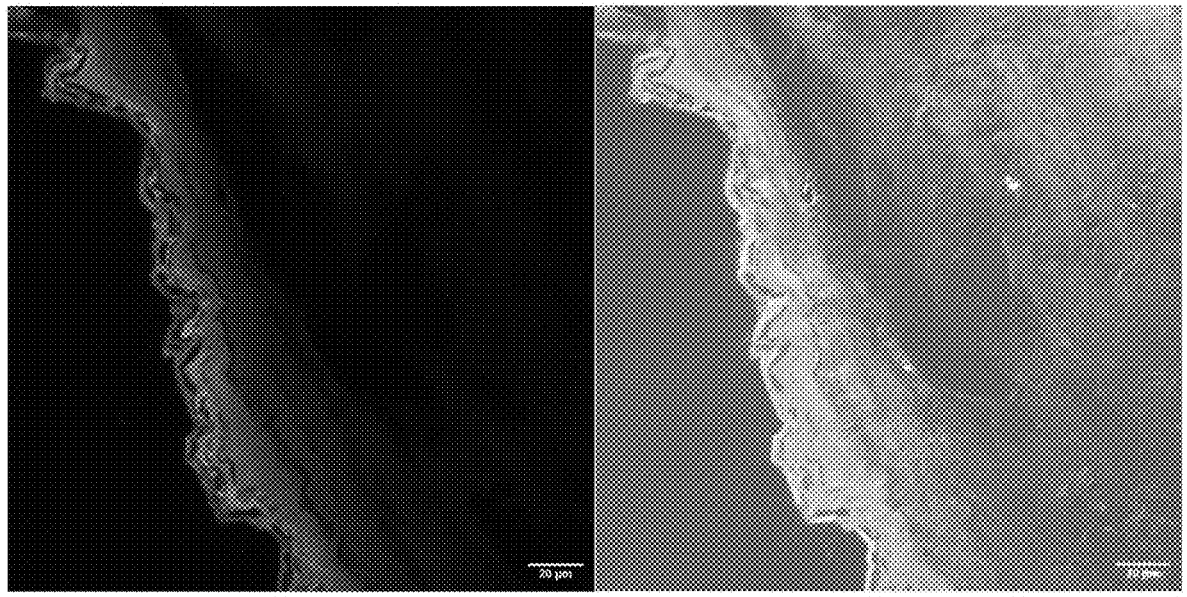
Fig. 32A                                    Fig. 32B

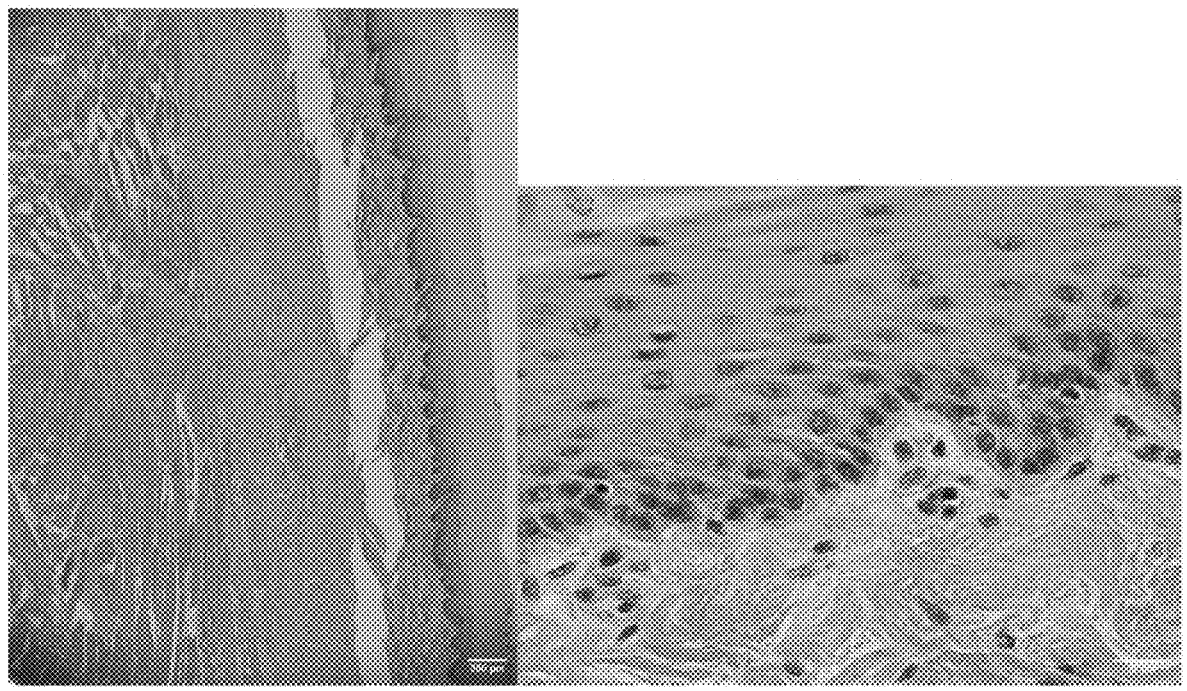
Fig. 33A                    Fig. 33B
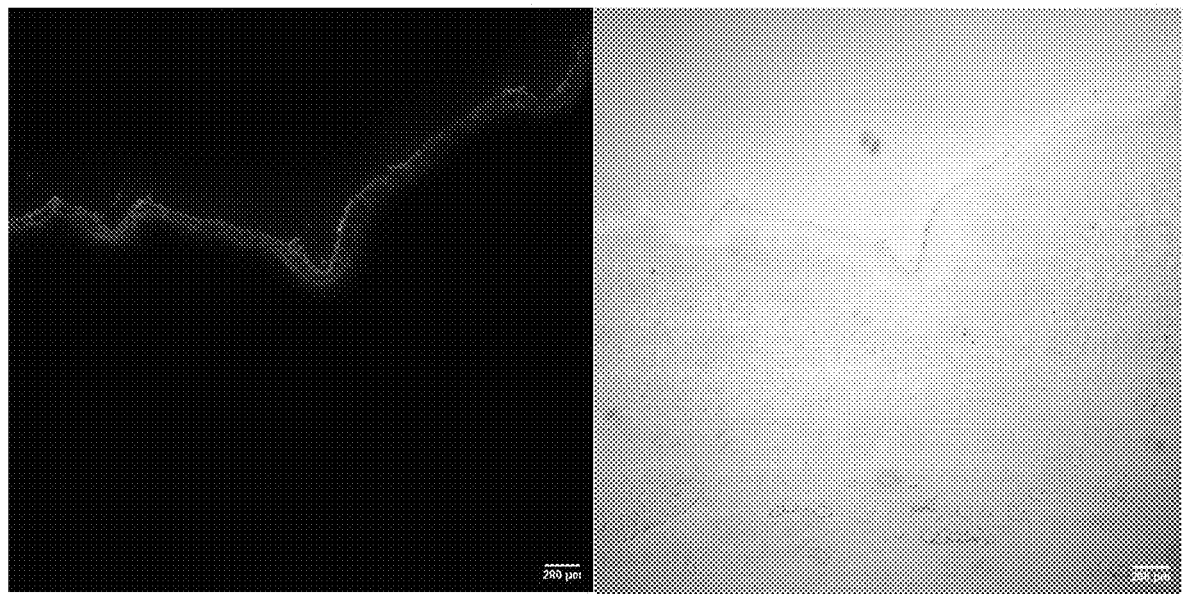
Fig. 34A                    Fig. 34B

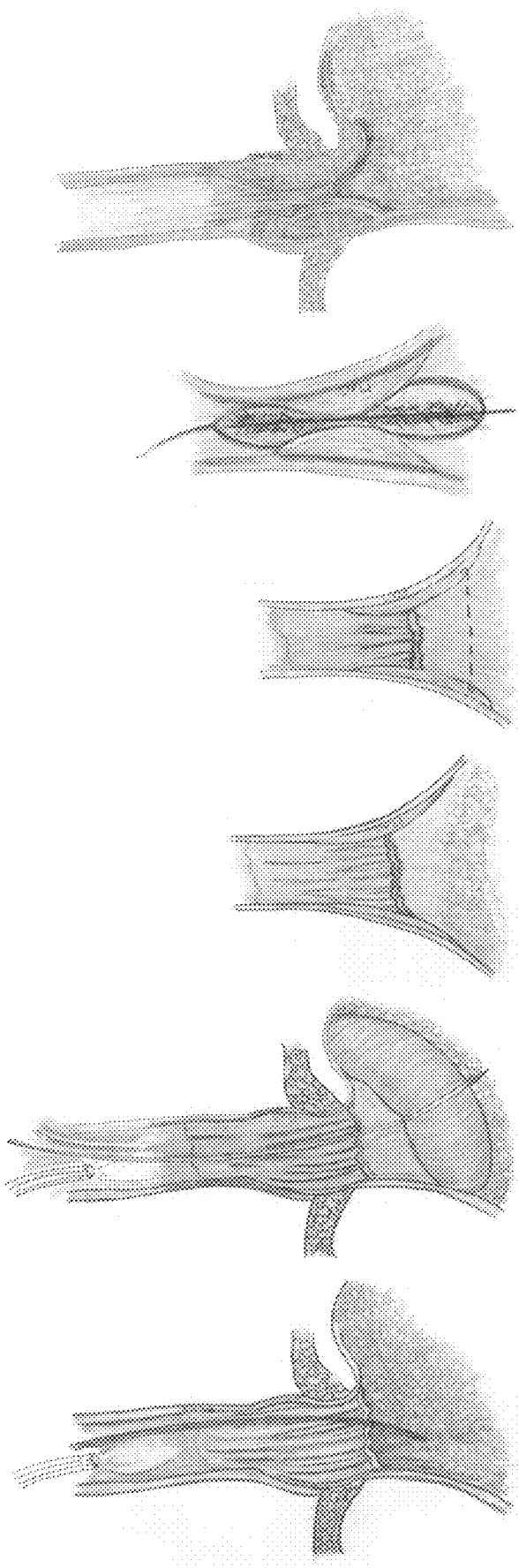

TREATMENT OF THE GASTROINTESTINAL TRACT WITH DIMERIC NAPHTHALIMIDE COMPOUNDS

RELATED APPLICATIONS

This application claims priority to provisional U.S. Application No. 63/395,854 filed on Aug. 7, 2022, the contents of which are incorporated herein by reference in their entirety for all purposes.

BACKGROUND

A stenosis typically refers to any point of narrowing of a channel that results from a structural abnormality. The gastrointestinal tract is a long muscular tube which functions to digest and absorb food and water. Muscles along the GI tract ensure the movement of food throughout the system, while mucosal secretions aid in digestion and adsorption of nutrients. There are four main layers to the digestive tract, namely the mucosa, submucosa, muscularis externa, and the adventitia or serosa. Within the gastrointestinal (GI) tract, a stenosis causes a partial obstruction or narrowing of the opening (lumen) in an area of the GI tract. A common form of stenosis is a stricture, which more specifically refers to a narrowing that results from a thickening of the wall of the GI tract. See, e.g., https://www.hopkinsmedicine.org/gastroenterology_hepatology/_pdfs/esophagus_stomach/swallowing_disorders. Gastrointestinal (GI) strictures cause problems by slowing or blocking the movement of food through the area. Common causes of GI strictures include recurrent inflammations, cancer, Crohn's disease, and ulcerative colitis. GI strictures may include esophageal strictures, achalasia strictures, biliary strictures, stomach strictures, small intestine strictures, duodenum strictures, jejunum strictures, ileum strictures, colon strictures, rectum strictures, and large intestine strictures.

One form of an esophageal stenosis, known as an esophageal stricture, is a problem commonly encountered in gastroenterological medicine. Esophageal strictures may occur as a result of muscular spasm, disease, notably gastroesophageal reflux disease, or injury such as accidental ingestion of caustic substances including strong acids and alkali. Esophageal strictures can be caused by malignant or benign lesions. Dysphagia, i.e., difficulty or discomfort in swallowing, is a symptom experienced by patients with esophageal strictures. Most of these patients require palliative treatment to relieve the dysphagia. The typical method of treatment is to physically dilate the region using a medical device (e.g., by way of fluoroscopically guided balloon) designed for that purpose. Following dilatation, an esophageal stent may be inserted to maintain the diameter of a stricture. However, a subset of the population is not responsive to balloon dilatation treatment, or other approved treatments. If dilatation fails or if stent placement is contraindicated, surgery is recommended.

A stenosis may occur in areas of the digestive system other than the GI tract. For example, a biliary stricture, also referred to as a bile duct stricture, occurs when the bile duct gets smaller or narrower. The bile duct is the tube that takes bile from the liver to the small intestine. When the bile duct becomes narrow, it makes it difficult for food to digest due to reduction in available bile. Biliary strictures can be caused by any injuries to the bile duct, swelling, pancreatitis, intestinal injuries, and cancers in the bile duct or pancreas. Common symptoms of a biliary stricture include pain, chills and fever, itching, and nausea or vomiting.

Since strictures are prone to reoccurrence, dilatation procedures have to be repeated. A need remains for therapies that inhibit loss of gain in a digestive (e.g., GI) lumen following a dilatation procedure, as well as non-surgical interventions that may alleviate stenosis without the need for concomitant dilatation.

BRIEF SUMMARY

A first aspect of the present disclosure is directed to a method of inhibiting loss of an increased lumen in an area of stenosis of the digestive system (e.g., gastrointestinal tract) following dilatation of the stenotic area in a subject, comprising administering to an area of the dilatation a composition comprising an effective amount of a dimeric naphthalimide, or a pharmaceutically acceptable salt thereof, and activating the dimeric naphthalimide via electromagnetic energy.

Another aspect of the present disclosure is directed to a method of increasing luminal diameter of an area of stenosis of the esophagus of a subject in need thereof, comprising administering to the area a composition comprising an effective amount of a dimeric naphthalimide, or a pharmaceutically acceptable salt thereof, and activating the dimeric naphthalimide via electromagnetic energy.

Yet another aspect of the present disclosure is directed to a method of restoring tone of the esophagus in a subject in need thereof, comprising administering to an area of the esophagus that exhibits irregular function, an effective amount of a dimeric naphthalimide, or a pharmaceutically acceptable salt thereof, and activating the dimeric naphthalimide via electromagnetic energy. In some embodiments, the area is the upper esophageal sphincter (UES). In some embodiments, the area is the lower esophageal sphincter (LES). In some embodiments, the subject has achalasia. In some embodiments, the subject has gastroesophageal reflux disease (GERD). Restoring tone to the area may normalize esophageal function.

A further aspect of the present disclosure is directed to a method of enhancing recovery of esophageal tissue following a surgical procedure, comprising administering to a subject at about the time of the surgical procedure, and at the site of the surgical procedure, a composition comprising an effective amount of a dimeric naphthalimide, or a pharmaceutically acceptable salt thereof, and activating the dimeric naphthalimide via electromagnetic energy.

The disclosed methods may eliminate the need for stents that tend to cause complications over time. Therefore, the dimeric naphthalimides may eliminate stenosed areas such as strictures, inhibit their reformation, and open closures of a treated area of the digestive system (e.g., GI tract) such as the esophagus without the use of implantable devices. The disclosed methods may be useful in treating any area of the digestive system such as the GI tract that is tubular in nature and prone or susceptible to stenosis (e.g., stricture formation) or otherwise exhibits irregular behavior or function.

As borne out in a working example, the esophagus is a relatively complex organ, compared to arteries, both in organization and function. A critically important function of the esophagus is peristalsis, a complex interplay of regions within the esophagus that allows swallowing. The present methods practiced in the context of the esophagus may restore this function.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 2A and B are endoscopic images of pre-insertion of saline with needle (A) and the injection of saline bolus (B).

FIGS. 3A-C are endoscopic illustrations of the resection process of a snare being used to cauterize the mucosa (A), the snare being used as lasso to remove resected mucosa (B), and the removal of remaining resected mucosa with Coagrasper (C).

FIG. 4 is an endoscopic illustration of the end of the EMR procedure on animal 19P39; resected mucosa with DA distending the lumen.

FIGS. 8A-C are endoscopic views of the esophageal stricture during treatment with the compound 1(a) (A), PTA balloon and light activation (B), and post treatment of the esophageal stricture (C).

FIGS. 9A-C are endoscopic views of the stricture site, taken on day 21 at 0 (A), 30 (B) and 60 (C) minutes after PTA balloon inflation.

FIGS. 10A-C are endoscopic views taken on day 21, during inflation with a PTA balloon, in increments of one-third (A), two-thirds (B) and full (C) at the stricture site (red arrow).

FIGS. 11A and B are endoscopic views of the esophageal stricture in animal 19P39 during to percutaneous transluminal angioplasty (PTA) (A) and post-PTA (B).

FIGS. 12A and B are endoscopic and fluoroscopic views of 19P41 28 days post treatment.

FIGS. 13A and B are endoscopic images at 21 days (before treatment) (A) and 28 days post treatment (B) of the stricture site in animal 19P37.

FIG. 14 is a photograph of an external view of the esophagus of animal 19P37 showing the stricture site 28 days post treatment.

FIG. 18 is a photograph of an internal view of the esophagus of animal 19P38 showing the stricture site 28 days post treatment.

FIGS. 19A-C are endoscopic images of contractions at the stricture site 28 days post treatment in animal 19P39.

FIG. 20 is a photograph of an external view of the esophagus of animal 19P39 showing minimal narrowing at the stricture site 28 days post treatment.

FIG. 21 is a photograph of an internal view of the esophagus of animal 19P39 showing the stricture site 28 days post treatment.

FIGS. 22A and B are endoscopic images of a distance view (A) and a close view (B) of the stricture site 28 days post treatment in animal 19P40.

FIG. 23 is a photograph of an external view of the esophagus of animal 19P40 showing the barely detectable stricture site 28 days post treatment.

FIG. 27 is a photograph of an internal view of the esophagus of animal 19P41 showing the irregular area of the stricture site 28 days post treatment.

FIGS. 28A and B are fluoroscopic representations of the stricture site (red arrow) in animals 19P38 (A) and 19P41 (B) 28 days post treatment. Animal 19P41 had minimal traces of a stricture.

FIGS. 29A and B are endoscopic images of the irregular stricture formation at day 21 in animal 19P41.

FIGS. 30A-F are a series of schematic diagrams illustrating an embodiment of the present invention to inhibit loss of an increased lumen in an area of stenosis of the gastrointestinal tract following dilatation of the stenotic area in a subject.

FIGS. 31A and B are light microscopy images of ex-vivo healthy swine arterial tissue cross-section; formalin fixed, paraffin embedded, and H&E stained; (A) image is at 10× magnification; and (B) is at 60× magnification focusing on the inner portion of the artery.

FIGS. 32A and B are fluorescence microscopy images of ex-vivo healthy swine arterial tissue cross-section delivered with 2 mg/mL 10-8-10 Dimer for five minutes; wherein (A) is a fluorescence image at 60× magnification and (B) is at 60× magnification with fluorescence and greyscale overlay.

FIGS. 33A and B are light microscopy images of ex-vivo healthy swine esophageal tissue cross-section; formalin fixed, paraffin embedded, and H&E stained; wherein (A) is at 4× magnification, and (B) is at 60× magnification focusing on the epithelial layer and lamina propria.

FIGS. 34A and B are fluorescence microscopy images of ex-vivo healthy swine esophageal tissue cross-section delivered with 4 mg/mL 10-8-10 Dimer for five minutes; wherein (A) is a fluorescence image at 4× magnification, and (B) is at 4× magnification with the fluorescence and greyscale overlay).

FIGS. 37A-F schematically illustrate an alternative embodiment of an endoscopic treatment for GERD.

DETAILED DESCRIPTION

Definitions

Figure 1:
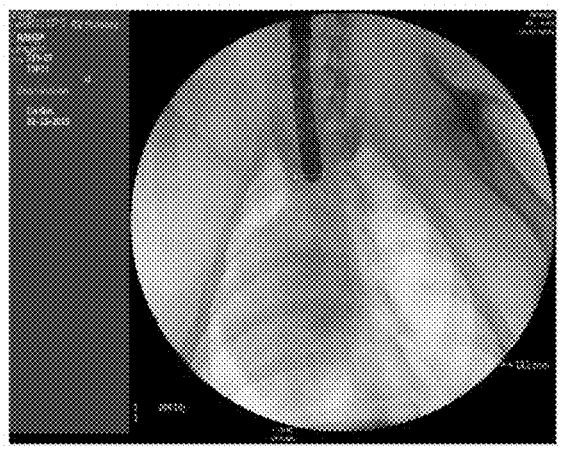
FIG. 1 is a day 0 fluoroscopy image (animal ID 19P39) that represents before endoscopic mucosal resection (EMR).

Unless defined otherwise, all technical and scientific terms used herein have the same meaning as is commonly understood by one of skill in art to which the subject matter herein belongs. As used in the specification and the appended claims, unless specified to the contrary, the following terms have the meaning indicated in order to facilitate the understanding of the disclosure.

As used in the description and the appended claims, the singular forms "a", "an", and "the" include plural referents unless the context clearly dictates otherwise. Thus, for example, reference to "a composition" includes mixtures of two or more such compositions, reference to "an inhibitor" includes mixtures of two or more such inhibitors, and the like.

Unless stated otherwise, the term "about" means within 10% (e.g., within 5%, 2% or 1%) of the particular value modified by the term "about."

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

In some aspects, the disclosed methods include treating areas of stenosis in the digestive system such as the GI tract. As used herein, "stenosis" refers to any point of narrowing of a channel or lumen in the digestive system e.g., GI tract that results from a structural abnormality. The narrowing causes a partial obstruction that results in a narrowing of the opening (lumen) in an area of the digestive system e.g., GI tract. As used herein, "stricture" is a specific type of stenosis that refers to a narrowing that results from a thickening of the wall of the digestive system e.g., GI tract. As used herein, the term "GI tract", also known as the alimentary canal, is a long tube that runs from the mouth to the anus. It includes the organs through which food and liquids travel when they are swallowed, digested, absorbed, and leave the body as feces. These organs include the mouth, esophagus, stomach, small intestine, large intestine, rectum and anus. The digestive system includes, in addition to the GI tract, accessory organs of digestion such as the liver, gallbladder and the pancreas. Areas of the digestive system that are also tubular in nature and susceptible to stenosis such as stricture formation such as the biliary canal, may be amenable to treatment with the disclosed methods.

In some embodiments, the inventive methods treat areas of stenosis in the upper GI tract such as the esophagus. Areas of stenosis may occur in the upper esophagus, middle esophagus and lower esophagus. All are treatable with the present methods.

In some embodiments, the area of stenosis contains a stricture. Strictures may arise in patients for a variety of reasons including muscular spasms, gastric/gastroesophageal reflux disease, have ingested caustic substances or as a result of benign or cancerous growths. These patients may benefit from the inventive methods. According to the American Society for Gastrointestinal Endoscopy, based on the diameter and associated anatomic abnormalities, an esophageal stricture can be classified as simple or complex. A simple stricture is defined as a short stricture with a symmetric or concentric lumen and a diameter of greater than 12 mm that can be traversed easily with an endoscope. A complex stricture is usually longer than 2 cm, may be angulated or irregular, and has a diameter of less than 12 mm. The severity of the stricture can be estimated by the resistance against the endoscope at passage through the esophagus. A mild stricture allows passage without resistance, a moderate stricture has some resistance, and a severe stricture may not be traversable with the endoscope.

In some embodiments, the area of stenosis is the lower esophageal sphincter (LES) that lies between the esophagus and the stomach. In normal digestion, the LES opens to allow food into the stomach. Then it closes to stop food and acidic stomach juices from flowing back into the esophagus.

In some embodiments, the area of stenosis contains an esophageal ring such as a Schatzki's ring, which also occurs in the lower esophagus.

Conditions, disorders and diseases associated with or caused by esophageal stenosis (e.g., strictures) that may be amenable to treatment with the disclosed methods include benign esophageal stricture, dysphagia lusoria, eosinophilic esophagitis (which if left untreated can result in esophageal stenosis and stricture formation), and severe forms of gastroesophageal reflux disease and achalasia (both disclosed in further detail below) that involve stricture formation.

In other embodiments, the inventive methods treat areas of stenosis in other parts of the upper GI tract including the stomach and the small intestine (which includes the duodenum, jejunum and ileum). In other embodiments, the inventive methods treat areas of stenosis in the lower GI tract including the large intestine (colon), rectum and anus. Representative examples of these types of non-esophageal stenosis include achalasia strictures, stomach strictures, small intestine strictures (including strictures of the duodenum, jejunum and ileum), rectum strictures, and large intestine strictures. These types of narrowing and their causes are also well characterized and may be diagnosed in accordance with standard techniques.

Areas of stenosis amenable to treatment with the disclosed methods may be located outside the GI tract but within the digestive tract. The bile duct is a tubular structure that takes bile from the liver to the small intestine. Strictures that may form in the bile duct are known as biliary strictures or bile duct strictures. This type of stricture causes the bile duct gets smaller or narrower which makes it difficult for food to digest. Biliary strictures can be caused by any injuries to the bile duct, swelling, pancreatitis, intestinal injuries, and cancers in the bile duct or pancreas. Symptoms of biliary strictures may include pain, chills and fever, itching, and nausea and vomiting.

Disclosed methods may be practiced in concert with a dilatation procedure, or not. To reiterate, upon activation, the dimeric naphthalimide compounds are believed to create a natural scaffolding in the walls of an area of stenosis (e.g., a stricture). In the case of being conducted in concert with a dilatation procedure, the natural scaffolding may inhibit loss of the increased lumen in the digestive system (e.g., GI tract) as a result of the dilatation. In the case of being conducted without a concomitant dilatation procedure, the natural scaffolding may inhibit further narrowing of the stenosis or substantially alleviate or eliminate the stenosis.

With respect to the latter, a patient may have a stricture that is recurrent and might have already been subjected to at least one dilatation procedure. The area of stenosis may be benign or cancerous in nature (e.g., esophageal cancer).

Yet another aspect of the present disclosure is directed to a method of restoring tone of the esophagus in a subject in need thereof, comprising administering to an area of the esophagus that exhibits irregular function (e.g., irregular tone), an effective amount of a dimeric naphthalimide, or a pharmaceutically acceptable salt thereof, and activating the dimeric naphthalimide via electromagnetic energy.

The term "tone" as used herein refers to sphincter function, esophageal wall stiffness and motility. Methods of measuring these properties are known in the art. See, e.g., Donnan, et al., Gastrolenterol. Clin. North Am. 49(3):427-35 (2020). Restoring tone to the affected area may normalize tone and esophageal function.

In some embodiments, the affected area is the lower esophageal sphincter (LES). The pressure in the LES depends on three factors: (1) the myogenic tone of the smooth muscles, (2) inhibitory nitrergic nerves, and (3) excitatory cholinergic nerves. The myogenic tone of smooth muscle is an intrinsic property of the cells in the LES and is responsible for its tonic contraction. The LES smooth muscle cells have a more depolarized resting membrane potentials, resulting in spontaneous spike-like action potentials and the generation of a basal tone. Excitatory cholinergic nerves release Ach (acetylcholine) to promote smooth muscle contraction, which enhances the tonic, myogenic property of the LES and favors contraction. In contrast, the nitrergic pathway releases nitric oxide and favors inhibition, opposing the contractile properties of the LES. Overall, the combination of these forces favors contraction over relaxation. Thus, the LES remains contracted even when entirely denervated owing to its myogenic property.

The primary function of the LES is the protection of the esophagus from highly acidic stomach secretions. Except in the lower one-eighth of the esophagus, the esophageal mucosa is not capable of resisting the digestive action of gastric secretions for a prolonged period. Under normal conditions, the LES remains tonically contracted with an intraluminal pressure of about 30 mmHg. When swallowing causes a peristaltic wave to pass down the esophagus, receptive relaxation of the LES occurs ahead of the peristalsis, allowing for easy propulsion of the swallowed bolus into the stomach.

The proper function of the LES occurs through two main mechanisms—myogenic and neural control. Myogenic control is the intrinsic rhythm of gastrointestinal smooth contraction and relaxation. Neural control is achieved through the autonomic and enteric nervous systems. The LES tonically contracts to an average pressure of 15 to 30 mmHg. After swallowing, inhibitory signals generated by peristalsis cause a reflex relaxation of the LES for approximately 5 seconds, allowing transit of the bolus into the stomach. During this time, the diaphragmatic crura also relax. After the bolus passage, the LES and crura return to their baseline contracted state. Transient LES relaxation (TLESR) is another physiologic relaxation of the LES that occurs outside of the swallowing mechanism. It is believed to be triggered by gastric distention and causes both the LES and the diaphragmatic crura to relax, allowing the release of excess gas. This process is followed by primary peristaltic waves distally to return any refluxed liquid into the stomach.

The disclosed methods are effective to treat an irregularly functioning LES, including both hypertensive and hypotensive LES, and associated conditions, disorders and diseases.

Hypertensive lower esophageal sphincters, for example, occur when the lower esophageal sphincter (LES) contracts tighter than normal or in a spasmic fashion. This causes the inability for foods or fluid to pass into the stomach normally. It can also create the inability to vomit or belch.

The disclosed methods may be effective to treat achalasia, which may be caused by an irregularly functioning, or hypertensive LES. Achalasia occurs when nerves in the esophagus become damaged. As a result, the esophagus becomes paralyzed and dilated over time and eventually loses the ability to squeeze food down into the stomach. Food then collects in the esophagus, sometimes fermenting and washing back up into the mouth, which can taste bitter. See, e.g., Paterson, et al., GI Motility online (2006) doi: 10.1038/gimo20, Published 16 May 2006.

In some embodiments, the present methods are effective to treat a condition, disorder or disease associated or caused by a hypotensive LES. In these situations, the LES is weak or relaxes when it should not, which enables the contents of the stomach to flow up into the esophagus. In some embodiments, the LES is targeted in a subject that has gastroesophageal reflux disease (GERD). See, Paterson, et al., supra. The most common symptom of GERD is heartburn. More than 60 million American adults experience heartburn, at least once a month. More than 15 million adults experience heartburn every day, including many pregnant women. Recent studies show that GERD in infants and children is more common than previously believed. It can cause vomiting that happens over and over again. It can also cause coughing and other breathing problems.

In some embodiments, the present methods are effective to treat a condition, disorder or disease associated with or caused by an irregularly functioning upper esophageal sphincter (UES). The upper esophageal sphincter (UES) serves a range of important physiologic functions. The UES provides a barrier against retrograde flow of digesta, and in so doing, serves an important protective function preventing aspiration of acidic gastric content into the respiratory tract. The sphincter also serves a barrier function by preventing the entry of air into the esophagus. The UES permits, by its physiologic relaxation, both antegrade and retrograde flow of material during swallowing, belching, and vomiting. See, Cook, et al., GI Motility online (2006) doi:10.1038/gimo37, Published 16 May 2006.

Yet other diseases, disorders and conditions that may be associated with or caused by an irregularly functioning esophagus that may be amenable to treatment with the disclosed methods include Barrett's esophagus, diffuse esophageal spasm, esophageal atresia, esophageal diverticula (e.g., Zenker's diverticula, which occurs at the top of the esophagus, mid-esophageal, which occurs in the middle, and ephiphrenic diverticula, which appear at the bottom), esophageal web, esophagitis, hiatal hernia, and laryngopharyngeal reflux (also known as Cricopharyngeal incoordination) and Nutcracker esophagus (both of which may occur separate and apart from GERD).

Yet other disclosed methods are relatively prophylactic in nature and also do not involve a dilatation procedure. Many esophageal procedures generate stenosis formation and/or loss of a degree of motility. Accordingly, the present methods may enhance recovery of esophageal tissue following these types of surgical procedures. Broadly, such methods entail administering to a subject at about the time of the surgical procedure, and at the site of the surgical procedure, a composition comprising an effective amount of a dimeric naphthalimide, or a pharmaceutically acceptable salt thereof, and activating the dimeric naphthalimide via electromagnetic energy. Representative examples of surgical procedures where the present methods may provide additional benefits include radiofrequency ablation, radiation therapy, endoscopic mucosal resection (EMR), esophageal stenting, endoscopic submucosal dissection (ESD), laparoscopic Heller myotomy (LHM), peroral endoscopic myotomy (POEM), endoscopic submucosal dissection (ESD), pneumatic dilation, diverticulectomy/myotomy, surgery to repair esophageal rupture, and electrocautery. Enhancement of recovery may entail any one or more of improved healing, increased esophageal motility, and inhibiting the onset of stenosis (e.g., strictures) in the surgical area.

The Dimeric Naphthalimides

Common to the inventive methods is the administration to a treatment area of the GI tract a therapeutically effective amount of a dimeric naphthalimide compound. As is known in the art, "dimeric" naphthalimides contain at least two 1,8-naphthalimide ring systems, joined by a spacer moiety or group.

In some embodiments, the dimeric naphthalimide is represented by any one of structures I, II and III:

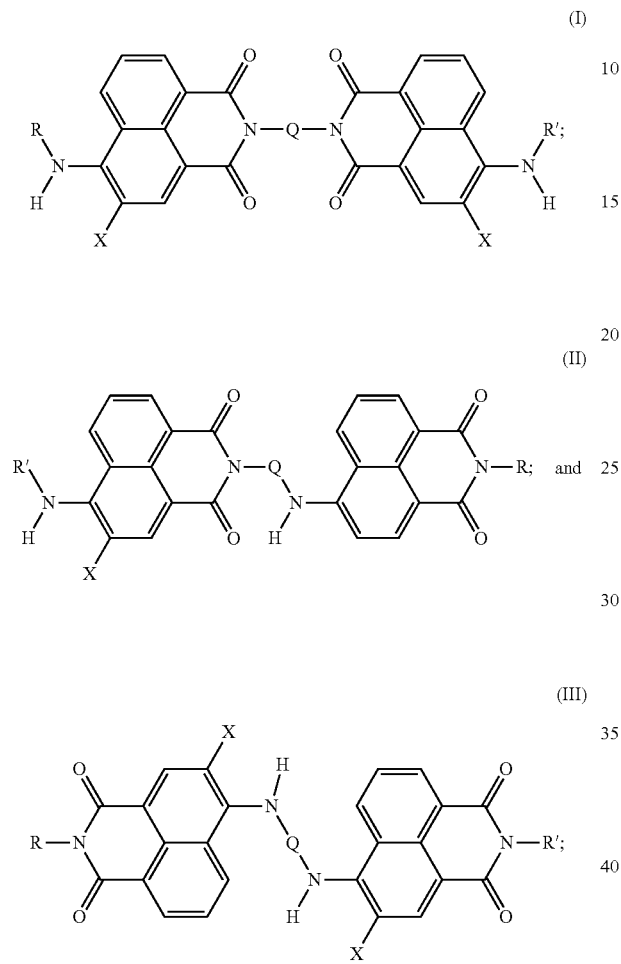

wherein R, R', and Q (also referred to as the spacer moiety) are each independently selected from the group consisting of straight-chain and branched chain alkyl groups having from 2 to 50 carbons, optionally substituted with one or more ether groups, one or more amide groups and/or amine groups; and wherein X is hydrogen, a halogen, a sulfonate ester or a quaternary ammonium salt.

In some embodiments, X is hydrogen.

In some embodiments, Q is a straight-chain or branched chain alkyl group having from 2 to 37 carbons, substituted with one or more ether groups. In some embodiments, Q is a straight-chain or branched chain alkyl group having from 2 to 25 carbons, substituted with one or more ether groups. In some embodiments, Q is a straight-chain or branched chain alkyl group having from 2 to 6 carbons, substituted with one or more ether groups.

In some embodiments, R and R' are each independently selected from the group consisting of straight-chain and branched chain alkyl groups having from 2 to 10 carbons, substituted with one or more ether groups and one or more amide or amine groups. In some embodiments, R and R' are each independently selected from the group consisting of straight-chain and branched chain alkyl groups having from 2 to 6 carbons, substituted with one or more ether groups and optionally substituted with one or more amide or amine groups.

In some embodiments, the dimeric naphthalimide is represented by structure Ia:

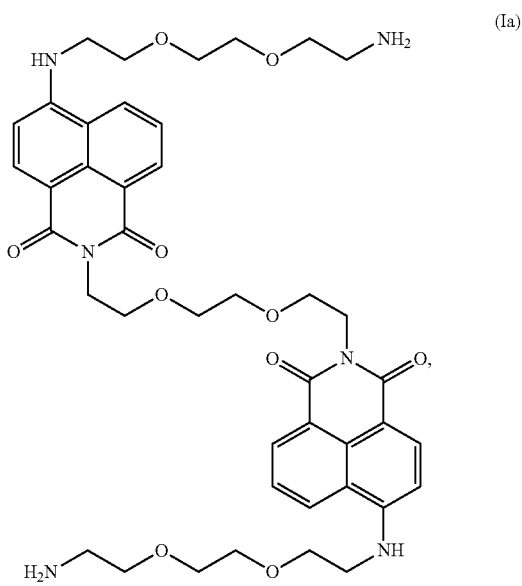 [SMILES: NCCOCCOCCNc1ccc2c3c(cccc13)C(=O)N(CCOCCOCCN1C(=O)c3cccc4c(NCCOCCOCCN)ccc(c34)C1=O)C2=O]

or a pharmaceutically acceptable salt thereof. This compound (in the form of a diacetate salt) was used in the experiments described in working example 1.

In some embodiments, the dimeric naphthalimide is represented by structure IIa:

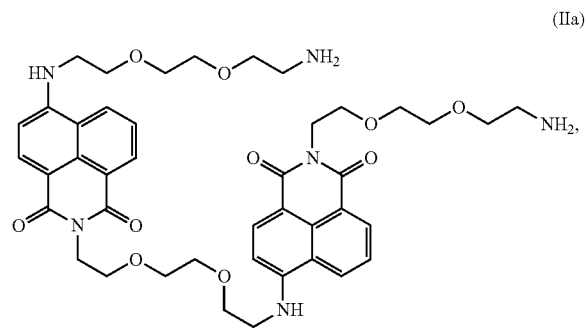 [SMILES: NCCOCCOCCNc1ccc2c3c(cccc13)C(=O)N(CCOCCOCCNc1ccc3c4c(cccc14)C(=O)N(CCOCCOCCN)C3=O)C2=O]

or a pharmaceutically acceptable salt thereof.

In some embodiments, the dimeric naphthalimide is represented by structure IIIa:

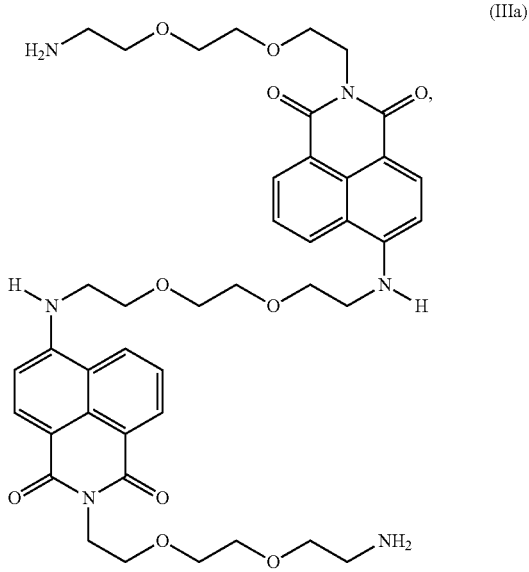 [SMILES: NCCOCCOCCN1C(=O)c2cccc3c(NCCOCCOCCNc4ccc5c6c(cccc46)C(=O)N(CCOCCOCCN)C5=O)ccc(c23)C1=O]

(IIIa)

or a pharmaceutically acceptable salt thereof.

The dimeric naphthalimide compounds may be in the form of a free acid or free base, or a pharmaceutically acceptable salt. As used herein, the term "pharmaceutically acceptable" in the context of a salt refers to a salt of the compound that does not abrogate the biological activity or properties of the compound, and is relatively non-toxic, i.e., the compound in salt form may be administered to a subject without causing undesirable biological effects (such as dizziness or gastric upset) or interacting in a deleterious manner with any of the other components of the composition in which it is contained. The term "pharmaceutically acceptable salt" refers to a product obtained by reaction of the disclosed compound with a suitable acid or a base. Examples of pharmaceutically acceptable salts of the compounds of this invention include those derived from suitable inorganic bases such as NaOH and CaO. Examples of pharmaceutically acceptable, nontoxic acid addition salts are salts of an amino group formed with inorganic acids such as hydrochloride, hydrobromide, hydroiodide, nitrate, sulfate, bisulfate, phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, 4-methylbenzenesulfonate or p-toluenesulfonate salts and the like.

The dimeric naphthalimides may be in the form of an isotopic derivative in that it has at least one desired isotopic substitution of an atom, at an amount above the natural abundance of the isotope, i.e., enriched. In one embodiment, the compound includes deuterium or multiple deuterium atoms. Substitution with heavier isotopes such as deuterium, i.e. 2H, may afford certain therapeutic advantages resulting from greater metabolic stability, for example, increased in vivo half-life or reduced dosage requirements, and thus may be advantageous in some circumstances.

Yet other dimeric naphthalimides that may be useful in the practice of the disclosed methods are described in U.S. Pat. Nos. 5,235,045; 5,565,551; 5,766,600; 5,917,045; and 6,410,505.

The dimeric naphthalimide may be formulated for administration to a treatment area in the GI tract in accordance with standard techniques and using carriers and/or excipients or diluents known in the pharmaceutical art.

In some embodiments of any of the disclosed methods, the compositions are in the form of liquids wherein the dimeric naphthalimide is substantially solubilized or dispersed therein. In some embodiments, the carrier is aqueous. Representative examples of aqueous carriers that may be useful in the practice of the present invention include water, saline, e.g., buffered saline (PBS) and isotonic solutions, e.g., Ringer's solution. In some embodiments, the carrier is non-aqueous. Representative examples of non-aqueous carriers that may be useful in the practice of the present invention include oils, e.g., vegetable oils, and organic solvents, e.g., alcohols such as ethanol, glycerol, and propylene glycol.

Liquid compositions may further include an excipient, representative examples of which include antioxidants/free radical scavengers, osmolarity agents, tonicity agents, pH modifiers or modulation agents, surfactants, viscosity agents, penetration enhancers, preservatives, and anti-proliferative agents.

Representative examples of antioxidants/free-radical scavengers include cysteine and derivatives, citric acid, benzoic acid, Ascorbic acid and derivatives, Caffeic acid and derivatives, Sodium metabisulfite, Propyl gallate, Gallic acid and derivatives, butylated hydroxytoluene, Butylated hydroxyanisole, Fatty acids e.g., oleic and linoleic acids, Terpenes e.g., eugenol, lycopene, and carotene (all forms) and terpenes e.g., tocopherol (all forms). The amount of the antioxidant is to inhibit degradation of the dimeric naphthalimide and/or inhibit impurity formation in the composition. In general, the antioxidant is present in an amount of about 0.005% to about 1.0%, e.g., about 0.5% to about 0.75%, based on the total weight of the composition.

Representative examples of osmolarity agents include pharmaceutically acceptable salts, e.g., acetate and citrate salts. Osmolarity agents, that are present to obligate water retention intraluminally to maintain isotonicity with plasma, may be present in a concentration of greater than 0 to about 1 Molar (M), e.g., about 140 millimolar.

Representative examples of tonicity agents include lactose, dextrose, sorbitol, mannitol, potassium chloride and sodium chloride. In general, tonicity agents may be present in the composition in an amount of about 0.25% to about 5.0%, based on the total weight of the composition.

Representative examples of pH modifiers include acetic acid, carbonic acid, citric acid, sodium bicarbonate, sodium hydroxide, sodium and potassium salts, e.g., sodium phosphate, potassium phosphate, sodium citrate, potassium citrate, sodium acetate and potassium acetate. The amount of the pH modifier is sufficient to achieve the desired pH. In general, the pH modifier is present in an amount of about 0.1% to about 2.5%, e.g., about 2%, based on the total weight of the composition.

Representative examples of surfactants include tocopherols, e.g., α-tocopherol, fixed oils, e.g., corn oil, cottonseed oil, peanut oil and sesame oil, polysorbate-20, polysorbate-80, and cyclodextrins, e.g., α-cyclodextrin and 2-hydroxypropyl-β-cyclodextrin. Surfactants, that may be present to increase the solubility of the dimeric naphthalimide in a liquid carrier, are typically present in an amount of 0.005% to about 10%, e.g., about 1% to about 10%, based on the total weight of the composition.

Representative examples of viscosity agents include celluloses (e.g., methyl cellulose, carboxymethyl cellulose, methylhydroxyethyl cellulose, methylhydroxypropyl cellulose, hydroxyethyl cellulose, hydroxypropyl cellulose, sodium carboxymethyl cellulose, and gelatin. The amount of the viscosity agent is sufficient to achieve the desired viscosity or thickness. In general, the viscosity agent is present in an amount of about 0.05% to about 2.5%, e.g., about 0.15% to about 0.25%, based on the total weight of the composition.

Representative examples of penetration enhancers include sodium oleate, diethylene glycol monoethyl ether, caprylic acid and benzyl alcohol. The amount of the penetration enhancer, that may increase the amount of the dimeric naphthalimide that is delivered to the GI tissue at the treatment area, typically ranges from about 0.01% to about 1.0%, based on the total weight of the composition.

Representative examples of imaging agents include radiographic imaging agents. These agents, which due to stability concerns, may be added to the composition about a day prior to and up to just prior to the administration of the composition to the subject.

Representative examples of preservatives that may be present to retard or inhibit microbial growth, include benzoic acid and derivatives, sodium benzoate, phenol and derivatives, C1-C6 alcohols and derivatives, benzylalkonium chloride and mixtures of methyl and propyl paraben.

Anti-proliferative agents may be added to the composition, prior to administration, typically about a day prior to immediately prior to administration. They may retard or inhibit proliferation of the GI tissue in the treatment area. Representative examples of anti-proliferative agents include paclitaxel and derivatives, rapamycin and derivatives (e.g., everolimus, tacrolimus, and zotarolimus) and pharmaceutically acceptable salts thereof. The anti-proliferative agent may be present with respect to the dimeric naphthalimide in a molar ratio of about 0.25:4 to about 4:0.25, e.g., 0.75:1.5 to about 1.25:1.5.

Liquid compositions have a volume that typically ranges from about 1 to about 20 milliliters (mL). In some embodiments, the volume of the liquid compositions is about 8 to about 12 mL. In some embodiments, the volume of the liquid compositions is about 10 mL.

In some embodiments, the compositions are administered in the form of solids. The dimeric naphthalimide may be formulated with pharmaceutically acceptable carriers, excipients and/or diluents, representative examples of which include glidants, lubricants, powdering agents, and disintegrants.

Representative examples of glidants include Magnesium silicate hydrate (talc), Magnesium stearate, Fumed silica/colloidal silica (Aerosil), Starch and N-Zorbit (tapioca maltodextrin).

Representative examples of lubricants include stearic acid, magnesium stearate, talc and silicon dioxide.

Representative examples of binding agents include starches, gelatin, acacia, alginic acid and pharmaceutically acceptable salts thereof and microcrystalline cellulose.

Representative examples of diluents (fillers) include calcium carbonate, calcium phosphate, lactose, mannitol and microcrystalline cellulose.

Representative examples of disintegrants include crospovidone, croscarmellose sodium and colloidal silica.

In some embodiments of any of the disclosed methods, the dimeric naphthalimide compound may be formulated in a coating composition that contains a carrier. The coating formulation may then be applied to the expandable surface (or portion thereof) of an expandable device such as a balloon catheter that is brought into contact with the treatment area in the GI tract. Representative examples of such carriers include poly(ethylene glycol), poly(vinyl pyrrolidone), phospholipids, fatty acids, sodium dodecyl sulfate, polysorbates, pluronics, cyclodextrins such as hydroxypropyl-beta-cyclodextrin, sucrose fatty acid monoesters, alkyl glycosides such as decyl maltoside and octyl maltoside, oleic acid, sorbitan trioleate, sorbital, mannitol, pectin, trehalose, tributyl citrate, triethyl citrate, glycerol monooleate, thymol, shellac, chitosan, collagen, elastin, silk, silk-elastin, alginate, cellulose, cellulosics such as hydroxypropyl cellulose, hydroxypropyl methylcellulose, methylcellulose, ethylcellulose, dextran, polyalkoanates, hyaluronic acid, gelatin, gellan, carrageenan, polylactide, poly(lactide-co-glycolide), poly(L-lactide-co-ca prolactone), polyglycolide, polyhydroxybutyrate, polyhydroxyvalerate, poly(ethylene glycol), polydioxanone, polyglactin, poly(E-caprolactone), polyglyconate, poly(glycolide-co-trimethylene carbonate), poly(sebacic acid), poly(ester urethane), poly(ester urethane) urea, cross-linked poly(ethylene glycol) (PEG), polyNIPAAM, PEG-poly(lactic acid) (PEG-PLA) block copolymers, and poloxamers.

In some embodiments, the carrier is polymeric, e.g., proteins, poly(lactic-co-glycolic) acid (PLGA), polyvinylpyrrolidone (PVP), polyethylene glycol (PEG), poloxamers and shellac. In some embodiments, the polymeric carrier is cross-linked. For example, shellac, modified shellac resins and shellac copolymers may be cross-linked using with urea, melamine, formaldehyde, and isocyanides.

A coating composition may be prepared by mixing the dimeric naphthalimide compound together with the carrier component(s), e.g., shellac, and a suitable solvent such as acetone, ethyl acetate, ethanol, methanol, DMSO, THF, chloroform, or methylene chloride. The resulting solution may be applied using conventional coating methods such as spray coating, dip coating etc. in order to obtain, after the drying step, a solid dimeric naphthalimide-carrier, e,g., shellac coating on the surface of the expandable device.

The amount of the dimeric naphthalimide per mm2 of a given device may vary given the variability in sizes of devices that may be used. In some embodiments, the coating composition is formulated so as to achieve a concentration of the dimeric naphthalimide on the surface of the device that ranges from about 1 to about 25 μg/ml. In some embodiments, the coating composition achieves a concentration of the dimeric naphthalimide on the surface of the device of about 7.5 μg/ml. The amount of the dimeric naphthalimide in the coating composition typically ranges from about 0.0001 to about 100 μg/ml. A representative example of a coating composition, exclusive of the dimeric naphthalimide, includes 90% EtOH/10% $H_2O$ and TRIS (e.g., in an amount of about 0.2 wt % relative to the dimeric naphthalimide).

In some embodiments, the coating composition may further include at least one other drug such as a painkiller, an anti-infective agent, or a chemotherapeutic agent.

Representative examples of local anesthetics include ropivacaine, mepivicaine, cocaine, procaine, lidocaine, hydrocodone, oxycodone and fentanyl, morphine.

Representative types of anti-infective agents generally include antibacterial agents, antifungal agents, antiparasitic agents, antiviral agents, antiseptics, iodine (e.g., povidone-iodine), potassium sorbate, sorbic acid, thimersol, thymol, butylene glycol, coconut oil, and vanillin. Anti-inflammatory agents generally include steroidal and nonsteroidal anti-inflammatory agents.

Representative examples of chemotherapeutic/antineoplastic agents include antitumor agents (e.g., cancer chemotherapeutic agents, biological response modifiers, vascularization inhibitors, hormone receptor blockers, cryotherapeutic agents or other agents that destroy or inhibit neoplasia or tumorigenesis) such as alkylating agents or other agents which directly kill cancer cells by attacking their DNA (e.g., cyclophosphamide, isophosphamide), nitrosoureas or other agents which kill cancer cells by inhibiting changes necessary for cellular DNA repair (e.g., carmustine (BCNU) and lomustine (CCNU)), antimetabolites or other agents that block cancer cell growth by interfering with certain cell functions, usually DNA synthesis (e.g., 6-mercaptopurine and 5-fluorouracil (5FU), anti-tumor antibiotics and other compounds that act by binding or intercalating DNA and preventing RNA synthesis (e.g., doxorubicin, daunorubicin, epirubicin, idarubicin, mitomycin-C and bleomycin), plant (vinca) alkaloids and other anti-tumor agents derived from plants (e.g., vincristine and vinblastine), steroid hormones, hormone inhibitors, hormone receptor antagonists and other agents which affect the growth of hormone-responsive cancers (e.g., tamoxifen, herceptin, aromatase inhibitors such as aminoglutethamide and formestane, triazole inhibitors such as letrozole and anastrazole, steroidal inhibitors such as exemestane), anti-angiogenic proteins, small molecules, gene therapies and/or other agents that inhibit angiogenesis or vascularization of tumors (e.g., meth-1, meth-2, thalidomide), bevacizumab (Avastin), squalamine, endostatin, angiostatin, Angiozyme, AE-941 (Neovastat), CC-5013 (Revimid), medi-522 (Vitaxin), 2-methoxyestradiol (2ME2, Panzem), carboxyami-dotriazole (CAI), combretastatin A4 prodrug (CA4P), SU6668, SU11248, BMS-275291, COL-3, EMD 121974, IMC-1C11, IM862, TNP-470, celecoxib (Celebrex), rofecoxib (Vioxx), interferon alpha, interleukin-12 (IL-12) or any of the compounds identified in Science Vol. 289, Pages 1197-1201 (Aug. 17, 2000), which is expressly incorporated herein by reference, biological response modifiers (e.g., interferon, bacillus calmette-guerin (BCG), monoclonal antibodies, interleukin 2, granulocyte colony stimulating factor (GCSF), etc.), PGDF receptor antagonists, herceptin, asparaginase, busulphan, carboplatin, cisplatin, carmustine, cchlorambucil, cytarabine, dacarbazine, etoposide, flucarbazine, flurouracil, gemcitabine, hydroxyurea, ifosphamide, irinotecan, lomustine, melphalan, mercaptopurine, methotrexate, thioguanine, thiotepa, tomudex, topotecan, treosulfan, vinblastine, vincristine, mitoazitrone, oxaliplatin, procarbazine, streptocin, paclitaxel, azathioprine, and docetaxel.

Carrier compositions for preparing compositions of drugs and methods of coating expandable surfaces of medical devices such as balloon catheters with the drug-containing compositions, are known in the art. See, e.g., U.S. Patent Application Publications 202000179659; 20200016377; 20200139020; 20190255300 and 20190255330 (which describes such a coating in the form of a biocompatible matrix may include a mixture of water insoluble and water-soluble materials, examples of which include shellac and polyvinylpyrollidone, and ethyl cellulose and hydroxypropylmethyl cellulose).

The pH of the composition may vary widely. Esophageal tissue, for example, is amenable to a broad pH range. In some embodiments, the pH of the composition ranges from about 2 to about 9. In some embodiments, the pH of the composition is about 6.

The compositions are formulated with an amount of the dimeric naphthalimide compound that is therapeutically effective. This amount is effective to initiate cross-linking of elastin and/or collagen present in the walls of the digestive (e.g., GI tract) to an extent that a natural scaffolding is created in the walls of an area of stenosis.

In some embodiments of any of the disclosed methods, the dimeric naphthalimide is present in the liquid composition in a concentration of about 4 to about 16 mg/ml. In some embodiments, the dimeric naphthalimide is present in the liquid composition in a concentration of about 4 to about 10 mg/ml. In some embodiments, the dimeric naphthalimide is present in the liquid composition in a concentration of about 4 to about 5 mg/ml.

In some embodiments with respect to solid compositions, the dimeric naphthalimide is present in the composition in a concentration of about 0.1 to about 1.0 milligrams (mg)/mg of the solid composition. In some embodiments, the dimeric naphthalimide is present in the solid composition in a concentration of about 0.3 to about 9.8 mg/mg, and in some other embodiments about 0.3 to about 9.5 mg/mg.

Some aspects of methods of the present disclosure entail a dilatation procedure. Methods and devices for dilating stenosed areas in the GI tract and tubular areas of the digestive system are known in the art. Balloon catheters, also known as balloon dilatation catheters, are but one type of medical device suitable for this purpose. Balloon dilatation catheters may be constructed of polyethylene (among other materials), and may be introduced, in deflated form, through the working channel of a previously placed endoscope or guide catheter or over a previously placed guidewire. For example, a physician may view the proximal end of a stenotic (e.g., stricture) site with an endoscope and introduce the balloon catheter with a deflated balloon into the narrowed area. The balloon is then inflated with saline or other physiologically acceptable and non-toxic fluid to effectively open or dilate the stenotic area such as a stricture site. Balloon dilatation catheters provide the advantages of multiple dilation diameters with a single intervention, passage through the working channel of an endoscope, and visualization of a stricture site from the proximal end. As the balloon inflates, it biases the stricture with a radial force, causing the tissue to stretch. A balloon dilatation catheter may be advantageous because it may be guidable over a previously placed guidewire or may have an internal wire for enhanced steerability, and, therefore may be more suitable for dilating smaller and/or tortuous areas of stenosis.

Another type of device is a bougie dilator, which may be advantageous in situations that call for both a shearing force and a radial force. Bougie tubes, in the form of a mercury- or tungsten-filled tube with a tapered end, may be used to gradually open a stenosed esophagus as it is pushed through and past the treatment site. These devices come in a series of increasing sizes, each tube having a single effective dilating diameter.

To the extent dilatation is conducted, the administration of the dimeric naphthalimide composition may be conducted prior to, concomitant with or subsequent to the dilatation procedure. Methods and devices for delivering pharmaceutically active agents to areas of the GI tract such as the esophagus are known in the art. For example, the composition containing the dimeric naphthalimide compound may be delivered endoscopically so as to fill the space above an inflated occlusion balloon or a non-inflatable device and the top of the stenotic area. The dimeric naphthalimide composition is allowed to be in contact with the walls of the treatment area for a time sufficient to allow the dimeric naphthalimide to penetrate the wall of the GI tract in the treatment area. In the case of liquid compositions and solid compositions alike, the contacting, e.g., soaking, is typically about 3 to 7 minutes, and in some embodiments about 3 to about 5 minutes. In the case of liquid compositions and solid compositions alike, the contacting, e.g., soaking, is typically about 5 minutes.

In some embodiments wherein the methods entail dilatation, two devices may be employed. A single balloon catheter, such as a Fogarty Occlusion Catheter, may be inserted into the treatment area, e.g., the esophagus, to prevent the liquid composition of the dimeric naphthalimide compound from entering the stomach. After soaking the treatment area, an appropriately sized dilatation balloon catheter, fitted with a guidewire lumen, may be inserted into the treatment area to provide dilatation. A light fiber may be inserted into the guidewire lumen and brought to the treatment area in order to provide the electromagnetic energy to activate the dimeric naphthalimide compound. All or a portion of the catheter shaft and balloon material must be transmissive to the electromagnetic energy used to activate the compound.

Other embodiments that entail dilatation may be practiced with a multifunctional catheter. For example, a single device may contain as many as three separately inflatable balloons, a first distal occlusion balloon for preventing the composition from entering the stomach, a second, more proximal occlusion balloon to prevent aspiration of the composition into the lungs, and a third, most proximal balloon for dilating the treatment area.

Following soaking, excess composition may be removed. The dimeric naphthalimide may then be activated via electromagnetic energy. Electromagnetic energy is a form of energy that is reflected or emitted from objects in the form of radiant waves that can travel through space; examples include radio waves, microwaves, infrared radiation, visible light, ultraviolet light, X-rays and gamma radiation.

Methods and devices for administering or delivering electromagnetic energy to areas in the GI tract are known in the art. For example, a balloon dilator may be equipped with a light fiber. An appropriately sized guidewire (e.g., 0.018 or 0.035 inches) may be inserted along the lumen of the guide catheter to the treatment area. This procedure may be conducted under fluoroscopy in order to confirm that the guidewire is suitably positioned in order to activate the dimeric naphthalimide compound.

In some embodiments of any of the disclosed methods, the electromagnetic energy is administered at an intensity of about 30 to about 100 mW/cm2 of treatment area. In some embodiments, the electromagnetic energy is administered at an intensity of about 35 mW/cm2 to about 40 mW/cm2 of treatment area, e.g., about 37 mW/cm2.

The activation is conducted with blue light (e.g., 400-500 nm). In some embodiments, the activation is conducted using a wavelength of about 440-460 nm. In some embodiments, the activation is conducted using a wavelength of about 445 to about 447 nm.

In some embodiments of any of the disclosed methods, the activation is conducted for about 1 to about 5 minutes. In some embodiments, the activation is conducted for about 1 to about 2 minutes. In some embodiments, the activation is conducted for about 1 minute.

In some aspects pertaining to treatment of the esophagus (which may or may not involve treating an area of stenosis (e.g., a stricture)), a liquid formulation of the dimeric naphthalimide compound or pharmaceutically acceptable salt thereof (e.g., a diacetate salt of the 10-8-10 dimer, is administered in a concentration of about 4 mg/ml, allowed to soak the esophageal tissue to which it is administered (the treatment area) for about 5 minutes, and then activated with electromagnetic energy at an intensity of about 35 mW/cm2 to about 40 mW/cm2 of treatment area using a wavelength of about 440-460 nm such as about 445 to about 447 nm.

These and other aspects of the present invention will be further appreciated upon consideration of the following Examples, which are intended to illustrate certain particular embodiments of the invention but are not intended to limit its scope as defined by the claims.

EXAMPLES

Example 1: Esophageal Stricture Formation and Treatment in Minipigs

Summary

This study investigated the use of naphthalimide based crosslinking chemistry for the treatment of esophageal strictures.

More specifically, this study evaluated the logistics for esophageal placement of compound I(a) with the use of contrast media, the crosslinking effects of compound I(a), and acute retention of dilation in an in vivo swine model.

It was shown that the delivery and retrieval of fluid to and from the esophagus can be accomplished economically with the use of commercially available devices, specifically an Edwards Fogarty occlusion catheter, commercially available from Edwards LifeSciences, Irvine CA, and a Cordis Vista Brite tip guiding catheter, commercially available from Cardinal Health, Santa Clara, CA 95054.

With the use of the endoscope and the above delivery/aspiration method compound I(a) penetration was observed and indications of potential crosslinking were seen at multiple sites.

An Olympus GIF-140 Endoscope was used in this study. Fluoroscopy was utilized throughout the procedures for confirmation of equipment placement, sample delivery, and removal.

Procedural Logistics for Esophageal Delivery

A 60-65 kg Yorkshire Cross (18P118) was used to establish the logistical techniques of the procedure. The animal was fasted for 24 hours prior to the procedure commencing. Post anesthesia swine 18P118 was positioned supinely (on its back) with the surgical table flat. A lavage was performed to flush any remaining contents from the esophagus and stomach. The endoscope was lubricated with a dime size amount of water based Astroglide and inserted into the mouth, passed by the epiglottis, around the pharyngeal diverticulum, through the esophagus and into the stomach. At insertion, the esophagus was partially open, (<5 mm diameter) circular and smooth. The esophagus formed around the catheter and the endoscope inserted instruments, ranging from 4 mm to 12.74 mm in diameter. The endoscope incremental measurements were used to determine the endoscope placement from the front incisor (zero reference point) to the lower esophageal sphincter (71 cm) with the designated working area being between 30 and 60 cm. The endoscope was maintained in the esophagus for the entire procedure.

Using the endoscope, the Edwards Fogarty occlusion catheter and the Vista Brite tip guide catheter were guided down the esophagus and positioned at the 45 cm mark. Positioning them simultaneously, then holding during inflation prevented slippage of the catheters during balloon inflation. The mucosa is loosely attached to the muscularis; the movement of any device in contact with the mucosa influenced the positioning of all inserted devices.

The 2 cm treatment zone was identified by starting with the endoscope against the top of the inflated occlusion balloon then retracting 2 cm. The guide catheter tip was then positioned even with the end of the endoscope per fluoroscopy. To provide better visibility of the delivery, while holding the occlusion and guide catheters in place, the endoscope was gently retracted about 1 cm. Contrast medium (50/50 mixture of Optiray 350 and saline) was delivered to the treatment zone (through the guide catheter). To accurately determine the volume required to fill the treatment zone the surgical table was tilted up approximately 20 degrees elevating the pig's head. This brought the fluid line closer to perpendicular within the esophagus. Once occlusion was confirmed the level of contrast medium in the treatment zone was brought to the end of the guide catheter yielding the volume (8 mL) required to fill the treatment zone.

Once the volume required to fill the treatment zone was determined the contrast medium was removed. In order to ensure the entire medium was removed the guide catheter was advanced to the lowest interface point between the balloon and esophagus. A syringe attached to the guide catheter was an efficient and effective means for aspirating all the contrast medium from the area.

It was noted that the active esophagus continually changes in shape, even when under anesthesia. As fluid flows into the esophagus, the esophagus increases in diameter and/or alters in shape from cylindrical to oval to flared (hourglass shaped) in order to accommodate and move the fluid.

Crosslink Healthy In Vivo Esophagus at Two Power Levels.

A second 60-65 kg Yorkshire Cross (18P119) was used to determine if a 10 mg/mL solution of compound I(a) would penetrate and crosslink esophageal tissue in a healthy swine in vivo esophagus. Treatment Site A: The procedural techniques developed for animal 18P118 were used in the subsequent animal, 18P119, to demonstrate the acute retention of gain. Following the aspiration of the contrast medium, both the occlusion and guide catheter were held in place as the endoscope was gently pulled back about 1 cm to allow visibility of treatment site A. The treatment zone was filled with 8 mL of compound I(a) (10 mg/mL in PBS) and allowed to soak for 10 minutes. During the soak period, the radially emitting light fiber was positioned within the dilatation/activation catheter. At the end of the soak time, excess compound I(a) was removed, and the occlusion balloon was deflated. The yellow coloration of the tissue is indicative of compound I(a) penetration.

The occlusion catheter was retracted slightly to prevent interference with the activation process. The catheter was positioned so the proximal end of the 4 cm balloon was located at the cranial end of the 2 cm treatment site. When in position the radially emitting light fiber was inserted into the catheter and aligned. The balloon was inflated in a three step process, 13.4 mm for 1 minute, 14.2 mm for 1 minute, and to the final size of 14.9 mm. The cooling drip was started, and the laser was turned on (74 mW/cm2). After 2 minutes, the laser and the drip were turned off and the balloon deflated. The catheter was moved out of the way for endoscopic and fluoroscopic imaging. The yellow coloration of the tissue is visible after activation.

Treatment of site B: The occlusion catheter was positioned within the esophagus and occlusion confirmed. The contrast dye was removed, and the guide catheter was positioned at the treatment zone. The occlusion and guide catheter were held in place as the endoscope was gently retracted to allow visibility of the treatment area. The treatment zone was filled with 8 mL of compound I(a) and allowed to soak for 10 minutes. At the end of the soak time, excess compound I(a) was removed, and the occlusion balloon deflated. The occlusion catheter was moved to prevent interference with the activation process. The yellow coloration of the tissue is indicative of compound I(a) penetration.

The dilatation/activation catheter was positioned fluoroscopically so the proximal end of the 4 cm balloon aligned with the cranial end of the 2 cm treatment site. When in position, light fiber alignment was confirmed.

The balloon was inflated in a three-step process. The cooling drip was started and the laser was turned on (32 mW/cm2) for 2 minutes. After 2 minutes, the laser was turned off and the balloon deflated. The catheter was moved out of the way and the site was imaged with the endoscope. The yellow coloration of the tissue is visible after activation.

The occlusion catheter and guide catheter were moved down to the site A location and positioned accordingly. The occlusion balloon was inflated, and the site was filled with contrast for imaging.

Treatment of site C: The use of a dual occlusion balloon catheter (TAPAS) was explored as an alternative delivery method. The proximal and distal occlusion balloons would contain the fluid to prevent potential aspiration. Due to the nature of the TAPAS catheter, a 14G guide wire was needed for the insertion into the esophagus. The guide catheter and dilatation/activation catheter was retracted out of the way. The distal occlusion balloon (DOB) was positioned at 35 cm and inflated, then the proximal occlusion balloon (POB) was positioned 2.5 cm above the distal balloon. The POB was filled partially, to prevent pressure buildup during the delivery process. A total of 10 mL of compound I(a) (10 mg/mL in PBS) was used, 2 mL to fill the TAPAS and 8 mL to fill the treatment site. When delivering compound I(a), resistance and back pressure were observed. The pressure was a potential concern because the automatic release valve within the TAPAS catheter is triggered by over pressurization releasing the fluid out the distal end of the catheter shaft. To prevent release of fluid, the fill rate and the size of the POB were reduced but reduction in resistance was not achieved and delivery continued. Compound I(a) was allowed to soak for 10 minutes. After the soak time, excess compound I(a) was removed, the occlusion balloons were deflated, and the TAPAS catheter was removed. The yellow coloration of the esophagus confirmed delivery despite the observed resistance.

The dilatation/activation catheter was positioned so the proximal end of the 4 cm balloon was aligned with the distal side of the POB. When in position, the radially emitting light fiber was aligned accordingly. The POB was inflated in a three-step process. The cooling drip was started, and the laser was turned on (32 mW/cm2) for 2 minutes. After 2 minutes, the laser was turned off and the balloon deflated. The catheter was removed, and the site was imaged with the endoscope. A gold/yellow tissue coloration was observed.

Post treatment: Prior to removal, the endoscope was advanced to the stomach to record the pull back of the entire esophagus. The esophagus was open at site A and had yellowish coloration. The esophagus between sites A and B closed right after the passing of the endoscope, and then opened again at site B. The esophagus closed between sites B and C then opened again at site C. Slight irritation was noted at site C. It is probable that this slight irritation was caused by the TAPAS catheter given the firm nature of the occlusion balloons. No significant irritation was noted the entire length of the esophagus on endoscopy or on necropsy examination. The opening at sites A, B and C indicate a crosslinking of the esophageal tissue.

Example 2: Esophageal Stricture Formation and Treatment with Compound I(a) Plus PTA with Light in Minipigs Introduction This 49-day study investigated the use of the technology on esophageal strictures generated by endoscopic mucosal resection (EMR) in healthy minipigs and demonstrated retention of dilation four weeks after being treated with compound I(a) crosslinking.

Day 0: Stricture Creation

Five healthy Yucatan minipigs (20-28 kg) were enrolled in the study. For the EMR procedure, each animal was monitored and maintained under anesthesia throughout the duration of the procedure. Each animal was placed in a supine position and elevated to a 5-12 degrees reverse Trendelenburg position, to aid in keeping gastric fluids from coming into the EMR procedural area. A water base lubricant (Astroglide) was used to aid at every insertion of the endoscope.

The upper GI was intubated and surveyed for abnormalities and gastric fluid content via a GIF-XQ140 endoscope. Of the five animals, three animals underwent lavage to remove excess fluid and debris from the esophagus and gastric lumen by washing with saline and suctioning out fluid/debris. A fluoroscopic esophagogram was taken of the target area with the endoscope in place (FIG. 1). The distal tip was measured with a calibrated digital caliper and the measurement was used to calibrate the fluoroscopic measurement tool. The esophageal diameter was measured and displayed. All representative fluoroscopic and endoscopic imagery are from animal 19P39 unless otherwise stated.

The target location was maintained during the EMR procedure by keeping the endoscope in the same axial position relative to the incisors.

The scope tip was positioned within ±3 cm of the target site. Suction was applied through the gastroscope to visualize the esophageal mucosa at the distal attachment (DA) and to visualize the injection range to capture approximately three-fourths of the esophageal lumen at the target site. The needle from the disposable EMR kit was inserted through the endoscope biopsy channel and into the endoscope field of view (FIG. 2A). The injector slider was pushed until it clicked into position to extend the needle from the sheath. A 10 mL syringe with saline was connected to the injector port. Suction was applied and the injector needle advanced to pierce the target mucosa and to inject a bolus of saline (FIG. 2B). The target area was injected with 0.5 mL to 2.0 mL of saline multiple times to reach a coverage of approximately three-fourths circumference of the target area. Following injections suction was released, and the needle withdrawn from the biopsy channel for insertion of the snare.

Figure 5:
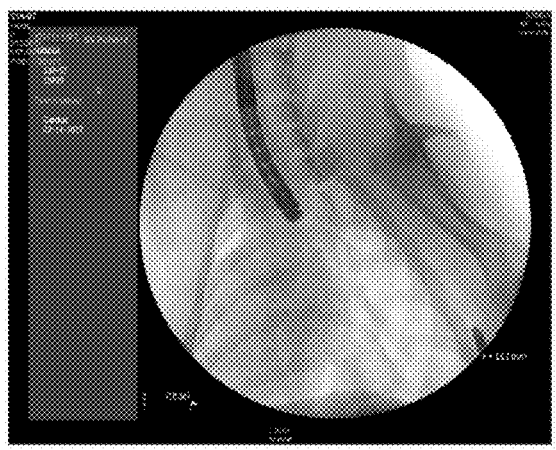
FIG. 5 is day 0 fluoroscopy image that represents (animal ID 19P39), post endoscopic mucosal resection post EMR.

The snare was used to remove the blistered mucosal tissue from the treated area. The snare was retracted and inserted into the biopsy channel and advanced into the field of view with the distal sheath. The snare was connected to the electrosurgical unit (Olympus PSD-20). The electrosurgical unit has two settings, one setting is CUT, which is used to cut the tissue and the other setting is COAG, which is used to cauterize the tissue. The snare loop tip was slowly extended approximately 5-10 mm beyond the DA, and CUT was activated marking the base of the tissue bolus by cauterizing the mucosa (FIG. 3A). Suction was used to draw the tissue bolus partially into the DA, and CUT was activated to separate the target mucosa from the submucosa/muscularis. The snare loop was also used as a lasso to remove the partially resected mucosa by cinching the snare closed around the resection (FIG. 3B) and activating the CUT pedal and COAG pedal as needed. The tissue that was not easily removed with the snare was removed with a coagrasper (FIG. 3C). The natural contraction movements of the esophagus posed some difficulty with maintaining a perfect depth to only exposing the submucosal tissue and to maintaining a consistent resection length throughout the resected area. For some animals there were portions of muscularis tissue exposed and some spiraling to the resected area due to the esophageal contractions (FIG. 4). Following the EMR a post procedural fluoroscopic esophagogram (FIG. 5) was taken and the animal recovered from anesthesia.

The EMR in the target area span approximately 270 degrees circumference and less than 2 cm wide.

Day 21: Stricture Evaluation

Figure 6:
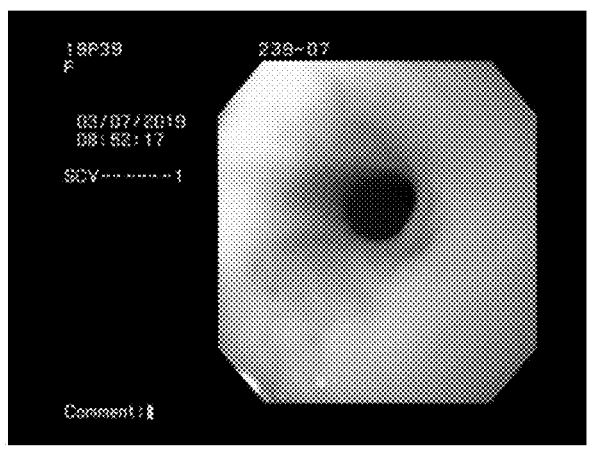
FIG. 6 is an endoscopic view of the esophageal stricture in animal 19P39 21 days post EMR.

On Day 21, post stricture induction, animals underwent anesthesia for evaluation of stricture formation and for stricture treatment. No lavage was needed to the esophagus or gastric lumen to complete the treatment on any of the animals. The table was generally tilted to 8 degrees elevating the minipigs' heads. The endoscopic visualization of the esophagus showed lack of muscle contraction and narrowing at the site of stricture formation for all animals (FIG. 6). There was also resistance felt on the endoscope at the entrance of the stricture. In order to prevent damage to the stricture from the endoscope, the endoscope was not passed through the stricture until completion of the treatment. The strictures produced in this study were classified as being in the complex category.

Figure 7:
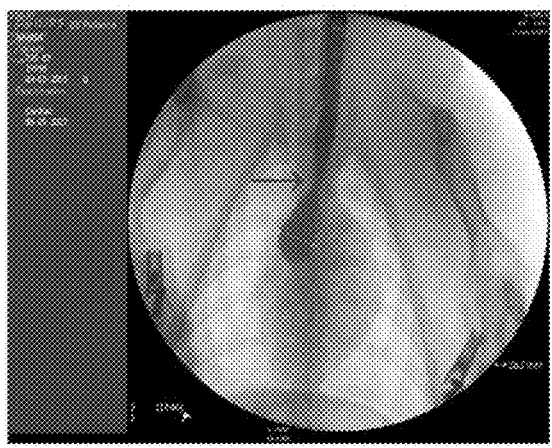
FIG. 7 is an endoscopic view taken on day 21, of the stricture (red arrow) in animal 19P39 before treatment.

The diameter of the endoscope tip was used to determine the size of the esophagus prior to treatment and post treatment. The endoscope was lubricated with a water base lubricant (Astroglide) prior to insertion, then followed by insertion of the 14F Fogarty Occlusion Catheter and the 10F Vista Brite Tip Guide Catheter. The occlusion and the guide catheter were simultaneously positioned below the stricture when possible. Some animals had a very active esophagus or tight epiglottis making passage difficult for simultaneous insertion. Once past the stricture, the occlusion balloon was inflated just enough to prevent fluid from leaking past the target area. The administration of the 50/50 (0.9% Sodium Chloride/74% Ioversol Injection) contrast through the guide catheter, and the balloon seal was observed under fluoroscopy and images were captured with measurements of the esophagus and the stricture location (FIG. 7), followed by contrast removal through the guide catheter.

Post-removal of contrast, animals were treated with the PTA balloon treatment (control) or with compound I(a) plus PTA with light. Throughout the treatment process, procedures were observed with fluoroscopic imaging and via endoscopic imaging.

Compound 1(a) Plus PTA Balloon with Light Treatment—Animals 19P37, 19P39 and 19P40.

Following the removal of the contrast, the occlusion balloon was left in place and the compound I(a) (10 mg/ml in PBS) was delivered to the stricture site with the guide catheter. The solution was sterilized upon delivery by filtering through a 0.22 μm syringe filter attached to the guide catheter. The volume of compound I(a) used was based on the volume needed to fill the stricture site. The tissue was soaked for 10 minutes prior to the solution being removed (FIG. 8A). The occlusion catheter was deflated and moved out of the way by pulling the catheter from the treatment site.

The guide catheter remained in place to pass the 0.035 guide wire past the stricture. Once the guide wire was in place the guide catheter was removed. Yellow coloration of the esophagus was observed indicating penetration.

The Percutaneous Transluminal Angioplasty (PTA) balloon catheter (Armada 35, 14.0 mm×40 mm×80 cm) was inserted over the guide wire, centering the balloon in the treatment area. A balloon longer than the EMR site was used to ensure coverage over the entire stricture area. The guide wire was removed from the PTA catheter and a 20 mm radially emitting light fiber was inserted in place of the guide wire. The cooling drip was turned on and the PTA balloon was gradually inflated, using a 20/30 Indeflator, in one-third increments (4, 6, and 8 atmospheres). Observations of the balloon inflation were done under fluoroscopy and observations for balloon slipping monitored. After each balloon inflation a hold time was implemented to allow the esophagus time to stretch. For the first two inflation increments, the balloon was held for one minute prior to the next inflation. During the last inflation, the laser was turned on (74 mW/cm2) for the hold period to light activate compound I(a) (FIG. 8B). Since the light fiber is half the length (20 mm) of the balloon two two-minute increments of light activation were conducted.

Once the light activation was complete, the PTA balloon was deflated. The light fiber was removed, and the guide wire was reinserted into the PTA catheter. The PTA catheter was removed (FIG. 8C), and the guide catheter was reinserted over the guide wire. Once in place, the guide wire was removed.

The occlusion balloon was positioned caudal to the stricture site and inflated enough to prevent leaking. Contrast was added to fill the treatment site for imaging purposes. After imaging the contrast-filled site, the contrast was removed through the guide catheter and the occlusion balloon was deflated. At thirty minutes and one-hour post treatment, the process was repeated. The occlusion balloon was inflated, contrast added, images taken, contrast removed, and the occlusion balloon deflated (FIGS. 9A-C).

Endoscope images were taken of the entire esophagus post removal of the catheters. Other than the stricture area, no abnormalities were seen in any of the animals via the endoscope imaging. Post removal of the endoscope, the animals recovered from anesthesia.

PTA Balloon Treatment Only—Animals 19P38 and 19P41

Following the removal of the contrast the occlusion balloon was deflated. The occlusion catheter was moved out of the way by pulling cranially from the treatment site. The guide catheter remained in place to pass the 0.035 guide wire past the stricture. Once the guide wire was in place the catheter was removed. The PTA catheter (Armada 35, 14.0 mm×40 mm×80 cm) was inserted over the guide wire, centering the balloon in the treatment area. A longer balloon was used to ensure coverage over the entire stricture area. The PTA balloon was gradually inflated, using a 20/30 Indeflator, in one-third increments (4, 6, and 8 atmospheres). Observations of the balloon inflation were done under fluoroscopy (FIGS. 10A-C). After each inflation, a hold time was implemented to allow the esophagus time to stretch. For the first two inflation increments, the balloon was held for one minute prior to the next inflation. Following the last inflation, the balloon was held for 3 minutes then the balloon was deflated, and the PTA catheter was removed. Damage to the esophageal wall was noted in the PTA balloon treatment group as shown for animal 19P38 (FIGS. 11A-B).

The guide catheter was reinserted over the guide wire to the treatment site. The occlusion balloon was repositioned below the treatment site and inflated just enough to prevent contrast from leaking past. The 50/50 contrast was administered to the treatment site through the guide catheter for fluoroscopic and endoscopic imaging. The contrast was removed, and the occlusion balloon deflated. Re-inflation of the occlusion balloon, addition of contrast, imaging, and occlusion balloon deflation were repeated at 30 minutes and at one-hour post PTA balloon treatment.

Endoscope images were taken of the entire esophagus post removal of the catheters. Other than the stricture area, no abnormalities were seen in any of the animals via endoscope imaging. Post removal of the endoscope, the animals recovered from anesthesia.

TABLE 2

Study Day 21 esophagus measurements made from fluoroscopic imagery, pre and post stricture treatment.

| | | Diameter of Stricture (mm) | | | | Esophagus diameter with inflated occlusion balloon | Length of Stricture (mm) | |
|---|---|---|---|---|---|---|---|---|
| Animal ID | Treatment | Pre-TX | 0 min. post TX | 30 min. post TX | 60 min. post TX | | Fluoroscopic Before TX | Endoscopic scan post TX |
| 19P37 | PTA + compound I(a) w/light | 2.9 | 15.88 | 17.13 | 13.8 | 20.0 | 10.4 | 30 |
| 19P38 | PTA | 6.9 | 12.64 | 12.35 | 10.5 | 21.4 | 9.8 | 20 |
| 19P39 | PTA + compound I(a) w/light | 4.9 | 13.0 | 7.5 | 8.5 | 20.2 | 14.7 | 17 |
| 19P40 | PTA + compound I(a) w/light | 3.8 | 12.4 | 14.8 | 10.9 | 25.3 | 19.1 | 30 |
| 19P41 | PTA | 6.5 | 7.7 | 7.0 | 8.3 | 18.9 | 16.3 | 10 |

Day 49: Tissue Harvest

On Day 49, animals underwent anesthesia for evaluation of the stricture treatment area. The table was tilted to 8 degrees in reverse Trendelenberg for all animals. The endoscope was passed through the esophagus, to the stricture site. The endoscope was used to take measurements from the animal's incisor to the opening of the stricture location. To prevent disturbance to the tissue, the endoscope was not passed through the stricture treated area except with animal 19P41. Animal 19P41 was the only animal where there was no resistance felt endoscopically and minimal visual observations were apparent at the stricture site, endoscopically and fluoroscopically (FIGS. 12 A and B).

Following the endoscopic scan, the occlusion balloon and guide catheter were inserted into the esophagus. The occlusion balloon was placed caudal to the stricture and inflated. A 50/50 contrast medium was delivered to the stricture area through the guide catheter. Fluoroscopic images and measurements were taken of the inflated occlusion balloon, stricture diameter and length (Table 3). Once the occlusion balloon was deflated fluoroscopic imagery and measurements were taken of the untreated esophagus diameter caudal to the occlusion balloon. After completion of imagery the surgical equipment was removed, the animal euthanized, and transported to necropsy. Heparin was administered intravenously prior to euthanasia to prevent post-mortem clotting.

TABLE 3

Study Day 49 (four weeks post treatment), fluoroscopic measurements comparing treatment stricture diameters before treatment and four weeks post treatment.

| Animal ID | Treatment | Diameter (mm) | | | | Length of Stricture (mm) Fluoroscopic |
|---|---|---|---|---|---|---|
| | | Diameter of Stricture Before-TX | Diameter of Stricture Post TX | Relaxed Esophagus Diameter Distal Balloon | Esophagus Diameter with Inflated Balloon | |
| 19P37 | compound I(a) + PTA w/light | 2.9 | 4.9 | 5.8 | 20.0 | 12.6 |
| 19P38 | PTA | 6.9 | 5.7 | 8.4 | 22.1 | 11.3 |
| 19P39 | compound I(a) + PTA w/light | 4.9 | 6.0 | 6.4 | 23.4 | 12.6 |
| 19P40 | PTA + compound I(a) w/light | 3.8 | 7.4 | 10.4 | 25.8 | 12.8 |
| 19P41 | PTA | 6.5 | 12.1 | 12.4 | 25.5 | 19.3 |

The prosector completed a gross examination of the esophagus to evaluate for abnormalities such as mucosal thickening, stricture formation size and location (Table 4), ulcerations, coloration, etc. The esophagus was excised, labeled, and photographed. The collected esophagus tissue was immersion fixed in 10% neutral buffered formalin and submitted for slide preparation and microscopic evaluation. General observations of the kidneys, liver, heart, and internal lining of the stomach showed no abnormalities.

TABLE 4

Study Day 49 Necropsy measurements (cross-section of esophagus) in millimeters.

| Animal ID | Treatment | Stricture Width | Stricture Length | Cranial to Stricture, Width | Caudal to Stricture, Width |
|---|---|---|---|---|---|
| 19P37 | compound I(a) + PTA w/ light | 7 | 25 | 20 | 17 |
| 19P38 | PTA | 11 | 25 | 25 | 24 |
| 19P39 | compound I(a) + PTA w/ light | 12 | 3-11 | 19 | 20 |
| 19P40 | compound I(a) + PTA w/ light | 10 | 5 | 21 | 23 |
| 19P41 | PTA | 7 | 15 | 20 | 20 |

Animal Observations

19P37

Figure 15:
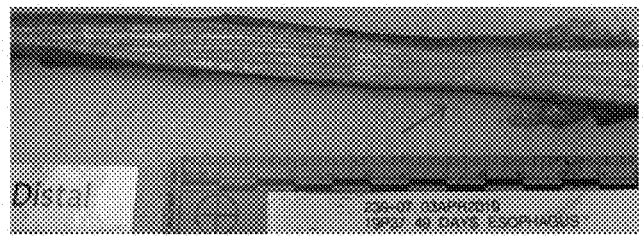
FIG. 15 is a photograph of an internal view of the esophagus of animal 19P37 showing the stricture site 28 days post treatment.

On day 49, evaluation of the treated stricture was completed. As the scope was being passed for the endoscopic scan of the esophagus, resistance was felt on the endoscope at 39 cm (cranial end of the stricture). Visual narrowing could be seen in the esophagus with the endoscope. The area appeared to be less rigid and have more movement/pliability than when it was viewed at 21 days. Mobility was still limited at the stricture but circular to oblong concentric rings that changed shape were present at the site (FIGS. 13A-B). As the contrast was added, fluoroscopic imagery showed narrowing of the esophagus. Necropsy observations of the external esophagus showed a slight palpable difference in the texture of the stricture (FIG. 14) in comparison to the healthy esophagus. With the esophagus opened in a longitudinal cross-section, the tissue at the stricture site was thicker than the rest of the esophagus tissue (FIG. 15). See Table 4 for tissue measurements.

19P38

Figure 16:
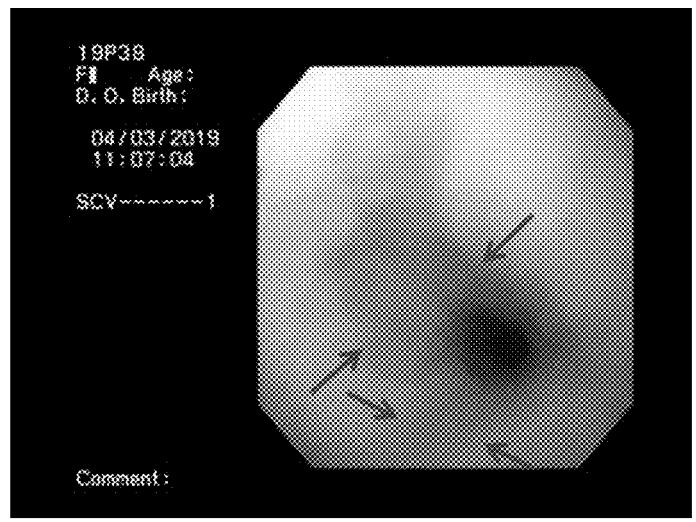
FIG. 16 is an endoscopic image of the stricture site in animal 19P38 28 days post treatment. The red arrows indicate areas of missing mucosa. and B are endoscopic images of a distance view (A) and a close view (B) of the stricture site in animal 19P3828 days post treatment.
Figure 17:
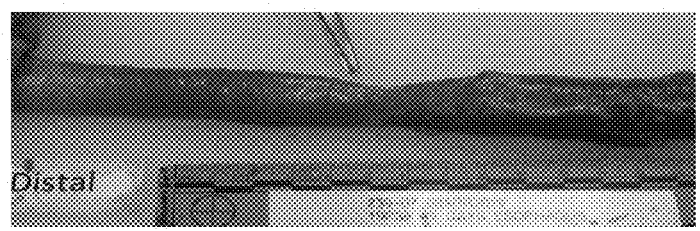
FIG. 17 is a photograph of an external view of the esophagus of animal 19P38 showing the stricture site 28 days post treatment.

On day 49, evaluation of the treated stricture was completed. As the scope was being passed for the endoscopic scan of the esophagus, resistance was felt on the endoscope at 40 cm (cranial end of the stricture). When examining the stricture site, with the endoscope, a large portion of the mucosa was missing (FIG. 16). The stricture did not appear to have any movement, it stayed open. Fluoroscopic imagery showed narrowing of the esophagus. Necropsy observations of the external esophagus view noted a slight palpable difference at the stricture, but the wall had a thinner feel than 19P37. A slight hourglass shape could be seen in the esophagus (FIG. 17). With the esophagus opened in a longitudinal cross-section the tissue at the stricture site was thicker and an hour-glass shape could be seen FIG. 18. See Table 4 for tissue measurements.

19P39

On day 49, evaluation of the treated stricture was completed. As the scope was being passed for the endoscopic scan of the esophagus, resistance was felt on the endoscope at 34.5 cm (cranial end of the stricture). The visual appearance of the stricture was distinctive and pliable with no scarring apparent. It was able to contract. Contractions were very apparent on respirations (FIGS. 19A-C). Concentric rings were apparent but did not appear to be at the degree of 19P37. Rings had a similar pattern as in animal 19P37. Fluoroscopic imagery showed narrowing of the esophagus.

No palpable difference could be felt externally on the esophagus at necropsy with very minimal visual narrowing in the esophagus (FIG. 20). With the esophagus opened in a longitudinal cross-section, the tissue at the stricture did not have any thickening or flat spots and was shorter in length than previous animals (FIG. 21). See Table 4 for tissue measurements.

19P40

Figure 24:
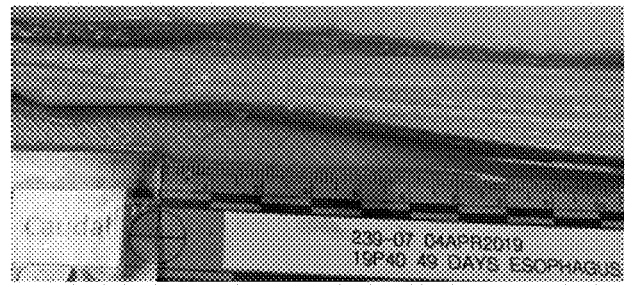
FIG. 24 is a photograph of an internal view of the esophagus of animal 19P40 showing the stricture site 28 days post treatment.

On day 49, evaluation of the treated stricture was completed. As the scope was being passed for the endoscopic scan of the esophagus, resistance was felt on the endoscope at 35 cm (cranial end of the stricture). The visual appearance of the stricture was circular and smoother in appearance with not as many concentric rings as seen in previous animals (FIGS. 22A-B). Fluoroscopic imagery showed narrowing of the esophagus. A subtle palpable difference at the stricture site was only detectable once the esophagus was completely extracted from the thoracic cavity at necropsy. A slight impression in the esophagus was visible (FIG. 23). When cutting the esophagus open, no thickened tissue was felt on the scissors when cutting through the stricture. The longitudinal cross-section of the esophagus showed striations through the esophagus and through the stricture site (FIG. 24). See Table 4 for tissue measurements.

19P41

Figure 25:
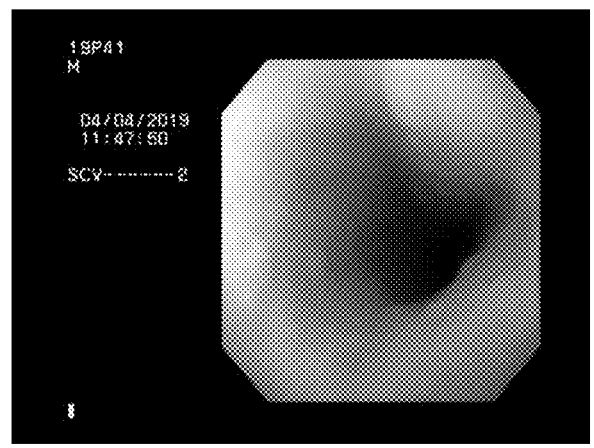
FIG. 25 is an endoscopic image of the stricture site 28 days post treatment in animal 19P41.
Figure 26:
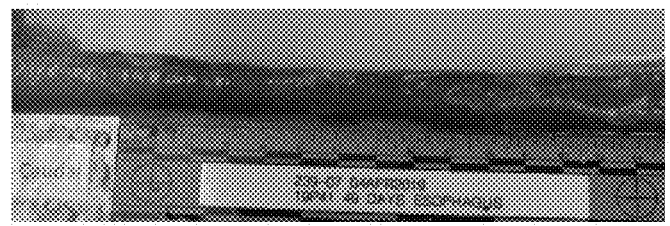
FIG. 26 is a photograph of an external view of the esophagus of animal 19P41 showing the stricture site 28 days post treatment.

On day 49, evaluation of the treated stricture was completed. For the endoscopic scan of the esophagus, as the scope was being passed no resistance was felt on the endoscope. The scope was passed all the way to the gastric opening and detracted slowly scanning for the stricture site. The caudal side of the stricture was determined to be at 34 cm. Visually, there were only remnants of the resection area present (FIG. 25). The tissue appeared pliable. When the Fogarty balloon was inflated for the addition of the contrast, there was little resistance felt on inflation of the balloon and the esophagus appeared larger in comparison with other animals. The fluoroscopic imagery showed very little narrowing of the esophagus. No tissue differences were palpable or visible on the excised esophagus, nor was there any noticeable difference in tissue thickness when the prosector cut the esophagus open (FIG. 26). The longitudinal cross-section of the esophagus showed irregular striations through the stricture site along with blotchy, raised sections of tissue (FIG. 27). See Table 4 for tissue measurements.

Conclusion

The differences between the stricture site and healthy esophagus tissue was evident in all animals. Due to the ongoing peristaltic contractions of the esophagus, comparison measurements between animals and animal groups were difficult to make. Some evidence appears to be notable at the stricture site with the diameter measurements prior to treatment to post treatment.

Significantly, all compound I(a) plus PTA balloon with light treated animals showed an increase in percent gain at the stricture site post-treatment, Table 10. PTA-only treated animal 19P38 showed a decrease of 17% post-treatment (FIG. 28A). PTA-only treated animal 19P41 displayed an anomalous result, a gain in the stricture site post treatment (FIG. 28B). This result is not expected in the literature or from our experience.

Animal 19P41 had cause for being an outlier. During the EMR procedure there was much difficulty performing the procedure due to an overactive esophagus. The stricture pattern gave an indication that the stricture formation may not have been complete throughout the EMR treated area.

Images in FIGS. 29A and B show gaps and lack of uniformity in the stricture ring. The mucosal wall had a very irregular tissue pattern that could be seen visually on the surface both with the endoscope and post necropsy.

TABLE 10

Percent of change in diameter of the stricture before and post treatment 29 days apart.

| Animal ID | Treatment | Diameter of Stricture Before TX | Diameter of Stricture Post TX | % Stricture Diameter Change Before and Post Treatment |
|---|---|---|---|---|
| 19P37 | compound I(a) + PTA w/light | 2.9 | 4.9 | 169% |
| 19P38 | PTA | 6.9 | 5.7 | −17.4% |
| 19P39 | compound I(a) + PTA w/light | 4.9 | 6.0 | 22.4% |
| 19P40 | compound I(a) + PTA w/light | 3.8 | 7.4 | 94.7% |
| 19P41 | PTA | 6.5 | 12.1 | 86.2% |

Visual observations were critical in determining the status of the resected area, stricture formation, movement, and function of the esophagus before and post treatment. The evidence indicates that compound I(a) plus PTA balloon with light treated animals had better success in restoring the esophagus to a healthier diameter and movement in comparison with the PTA balloon only treatment (19P38).

The pathology report confirmed areas of esophageal stricture were present microscopically for all animals. The microscopic appearance of the stricture sites was similar for all animals in both groups. Re-epithelialization was complete for all compound I(a) plus PTA balloon with light treatment but not for the PTA balloon treated animal 19P38. The anomalous PTA balloon treated animal, 19P41, was also re-epithelized. The observations indicated that all animals exhibited re-epithelialization with varying degrees of thickness at sites B and C. There were no procedure-related microscopic observations in the esophagus cranial or caudal to the stricture.

CITATIONS

1. Blount, K., Lambert, D., Shaffer, H. & de Lange, E. Fluoroscopically Guided Balloon Dilation of the Esophagus. Semin. Interv. Radiol. 27, 232-240 (2010).
2. Hwang, J. C. et al. Esophageal stricture induced by an ultraslim upper endoscope in a novel rabbit model of corrosive injury. Scand. J. Gastroenterol. 49, 30-34 (2013).

Example 2: Illustration of Inhibition of Loss of an Increased Lumen in an Area of Stenosis of the Gastrointestinal Tract Following Dilatation of the Stenotic Area in a Human Subject The following procedure is prophetic in nature with the following steps anticipated. As illustrated in FIG. 30A, the area of stenosis may be viewed with an esophageal endoscope in order to position and inflate an occlusion balloon caudal to treatment area containing the esophageal stenosis.

As illustrated in FIG. 30B, the occlusion balloon is inflated in order to fill the cranial portion of the esophagus with fluid to ensure occlusion.

Figure 30C:
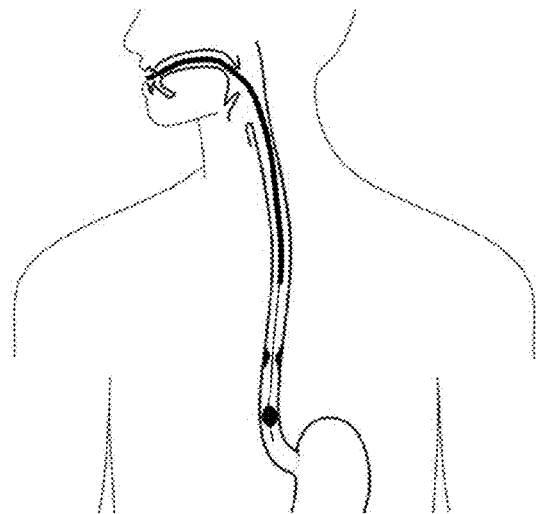

As illustrated in FIG. 30C, the fluid is aspirated through the esophageal scope.

Figure 30D:
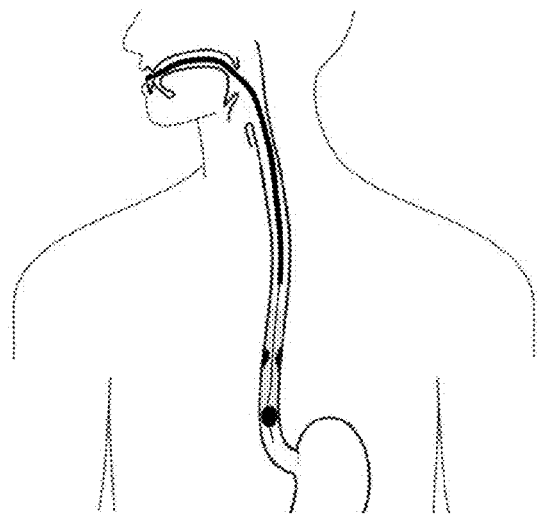

As illustrated in FIG. 30D, the treatment area is filled with a liquid composition containing the dimeric naphthalimide followed by soaking for about 5 minutes. The soaking allows the dimeric naphthalimide (e.g., about 10 mL of the composition containing about 4.0 mg/mL of the compound) to penetrate the esophageal wall.

Figure 30E:
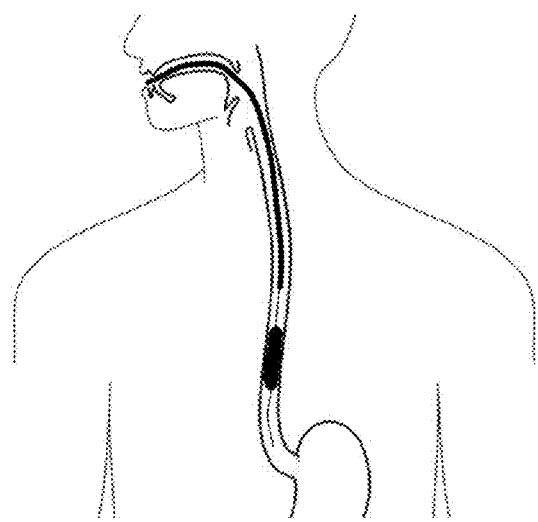

As illustrated in FIG. 30E, a CRE PRO Wireguided Balloon Dilatation Catheter, commercially available from Boston Scientific Corporation, Marlborough, MA, USA, is placed in the treatment area, followed by esophageal dilatation in accordance with manufacturer's instructions.

Figure 30F:
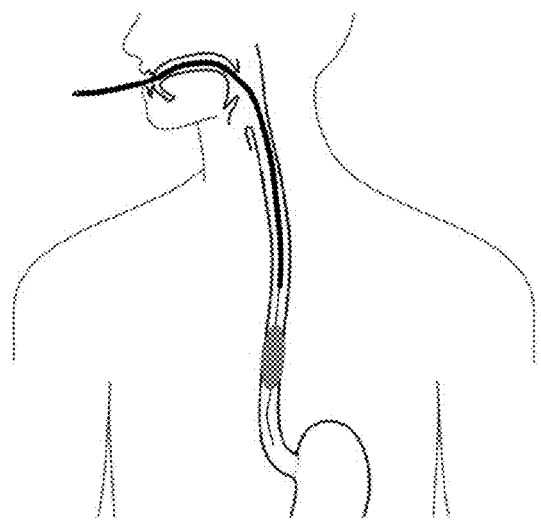

As illustrated in FIG. 30F, during the final dilation while the balloon is still inflated, a light fiber is inserted into the CRE PRO balloon catheter and advanced to the treatment site. Blue light, which may be administered at 40 mW/cm2 for about two minutes, activates the dimeric naphthalimide compound. The esophageal dilatation balloon is deflated and the catheter is removed. The dilated area may be viewed via endoscopy.

Example 3: Comparison Between Arterial and Esophageal Tissue Following Administration of 10-8-10 Dimer Arterial tissue throughout the body has three main layers: tunica interna, tunica media, and tunica externa. As shown in FIG. 31A, the lumen is at the left of the image. A single line of endothelial cells lines the lumen, with an internal elastic lamina (IEL) between the intima and the media of the tissue. A more magnified image shown in FIG. 31B displays the simple endothelium and the pink band of the IEL between the intima and the media. The tunica media takes up a majority of the artery and contains significant portion of collagen, elastin, and smooth muscle cells.

FIGS. 32A and B are 60× fluorescence microscopy images of ex-vivo healthy swine arterial tissue cross-sections treated with 2 mg/mL 10-8-10 Dimer for five minutes; wherein (A) is a fluorescence image and (B) is a fluorescence and greyscale overlay. As shown, the 10-8-10 Dimer penetrated through the arterial intima and into the media. The single layer of endothelium did not inhibit penetration of the 10-8-10 Dimer, and the somewhat uniform tunica media allowed further penetration throughout a vast portion of the tissue matrix.

FIGS. 33A and B show the histology of an esophagus. More specifically, FIGS. 33A and B are light microscopy images of ex-vivo healthy swine esophageal tissue cross-section; formalin fixed, paraffin embedded, and H&E stained; wherein (A) is at 4× magnification, and (B) is at 60× magnification focusing on the dense epithelial layer and lamina propria. In FIG. 33A the lumen is on the right side with a thick epithelium leading up to the basement membrane (purple line) followed by the lamina propria, muscularis mucosa, submucosa, muscularis propria, and adventitia. The white area in the middle of the tissue is artefactual. Not pictured in the image is the longitudinal layer of muscle in the muscularis propria as well as the adventitia. The epithelium, lamina propria which contains dense irregular connective tissue, and the muscularis mucosae make up the mucosa. Following is the submucosa which contains mucus glands and ducts. FIG. 33A also shows a layer of circular muscle cells which is the inner layer of the muscularis propria (left). The muscularis externa composition changes throughout the esophagus from skeletal muscle to smooth muscle. Richter, J. E.; Castell, D. O. The esophagus; Wiley Blackwell: Chichester, 2021 FIG. 33B shows the area near the lumen (top) with the stratified squamous epithelium, basement membrane, and lamina propria. Overall, the esophageal tissue is much thicker than the arterial tissue, with very distinct sections. Part of this thickness is due to the thick epithelial layer in the esophagus.

FIGS. 34A and B are 4× fluorescence microscopy images of ex-vivo healthy swine esophageal tissue cross-section treated with 4 mg/mL 10-8-10 Dimer for five minutes; wherein (A) is a fluorescence image, and (B) is the fluorescence and greyscale overlay. As shown therein, The penetration of 10-8-10 Dimer into ex-vivo esophageal tissue is also vastly different from arterial tissue penetration. As shown therein, the preponderance of 10-8-10 Dimer fluorescence is in the epithelium; there was no significant fluorescence in the submucosa or muscularis. Treatment with 2 mg/ml of 10-8-10 Dimer was ineffective. In contrast to the treatment of arterial tissue, the 10-8-10 Dimer was efficacious at a concentration 100% greater.

Example 4: Treatment of Achalasia and HLES

Figure 35E:
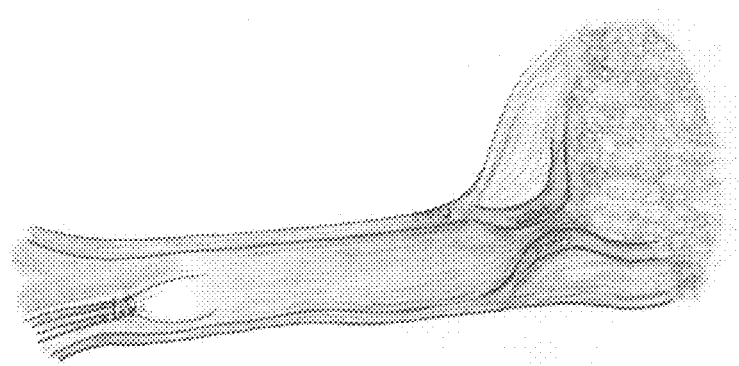
FIGS. 35A-E schematically illustrate an endoscopic treatment for achalasia and HLES.
Figure 35D:
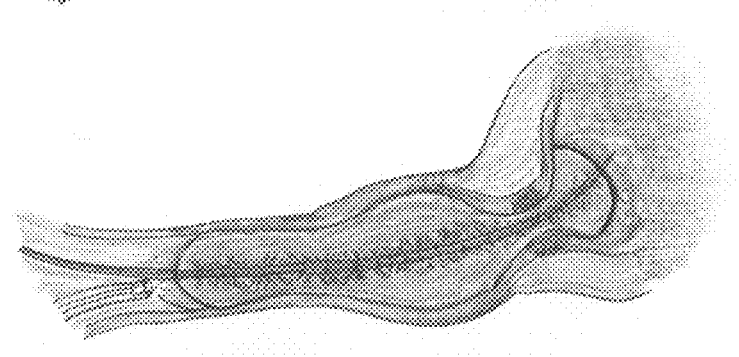
Figure 35C:
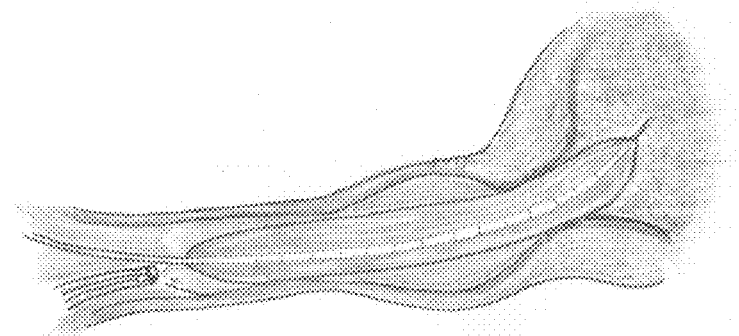
Figure 35B:
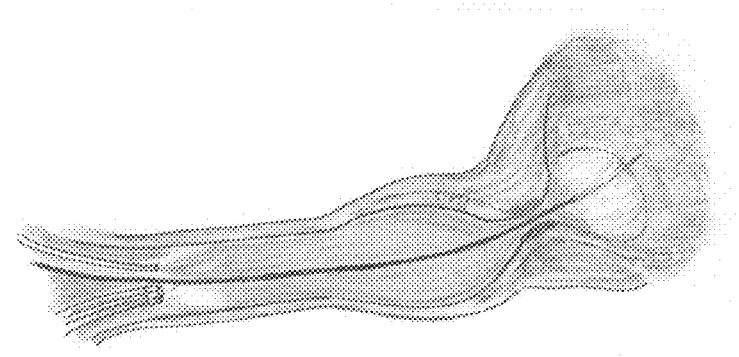
Figure 35A:
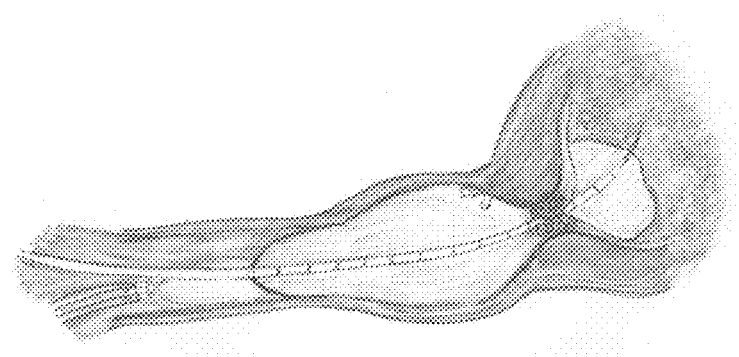

FIGS. 35A-E schematically illustrate an embodiment of an endoscopic treatment for achalasia and HLES. As shown in FIG. 35A, treatment preparation may assess motility and distention of the lower esophagus and LES with appropriate technology such as EndoFLIP. The length of enlarged portion of the esophagus and the pressure within the LES are determined. As shown in FIG. 35B, the EndoFLIP catheter is removed and an occlusion balloon catheter and a guide catheter are inserted. The occlusion balloon is positioned below the LES in the stomach. The occlusion balloon is gently inflated, just enough to prevent fluid leakage. The guide catheter is positioned below the LES near the occlusion balloon. The 10-8-10 dimeric naphthalimide composition (e.g., solution) is slowly delivered through the guide catheter to the treatment area, from the bottom of the LES to above the distended esophagus, ensuring all air bubbles are removed. As shown in FIG. 35C, the treatment area is then soaked with the dimeric naphthalimide composition for an appropriate time. During the soak (not shown), the dilatation/activation catheter and light fiber are prepared. After the soak, as much of the 10-8-10 dimeric naphthalimide composition is solution as possible is removed through the guide catheter. The occlusion balloon is deflated, and deflation is confirmed fluoroscopically and endoscopically. The occlusion balloon catheter is removed or positioned out of the way for activation by moving it above the treatment site. A determination is made as to the required stretch to achieve the desired LES apposition pressure, while allowing tone to return to the lower esophagus. If a great deal of pressure is required to stretch the LES, the dilated esophagus may be treated by a separate step to prevent unwanted distention. As shown in FIG. 35D, a dilatation/activation catheter, such as an Esoflip, is inserted past the LES. The balloon is centered over the treatment site, beginning of distention past the LES into the stomach. The light fiber is inserted into the catheter, and the dilatation/activation balloon is gradually inflated to the desired size and hold, following by activation for the desired time. As shown in FIG. 35E, at the completion of the procedure the esophageal tone is restored as well as the appropriate LES pressure.

Example 5: Treatment of Gastroesophageal Reflux Disease (GERD)

Embodiments of the disclosed methods in the context of treating GERD are illustrated in FIGS. 36 and 37. As shown in FIGS. 36A and 37A, the motility (function) and tone (strength) of the esophagus and the abnormally thinned LES are assessed to determine the extent of the damage. One of the causes of the over extension of the LES is due to high stomach pressure for an extended period of time. As shown in FIGS. 36B and 37B, an occlusion balloon is positioned below the lower distended ends of the LES in the stomach and inflated, ensuring that the entire LES is available for treatment. The guide catheter is positioned below the LES near the occlusion balloon. The 10-8-10 dimeric naphthalimide composition (e.g., solution) is delivered through the guide catheter to the treatment area, which extends from the bottom of the LES to above the damaged esophageal area. FIGS. 36C and 37C show the penetration of the 10-8-10 dimeric naphthalimide composition into the distended LES.

Figure 36F:
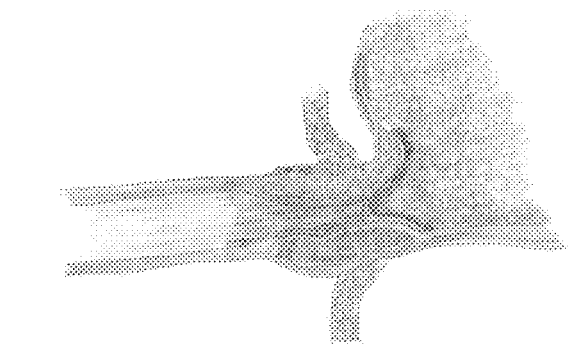
FIGS. 36A-F schematically illustrate an embodiment of an endoscopic treatment for gastroesophageal reflux disease (GERD).
Figure 36E:
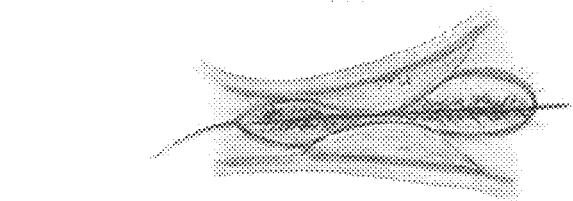
Figure 36D:
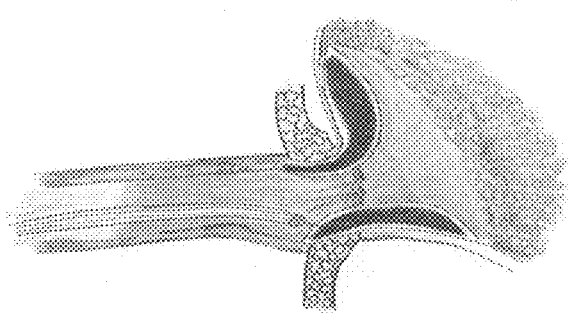
Figure 36C:
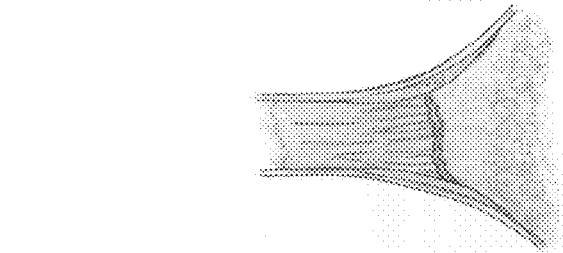
Figure 36B:
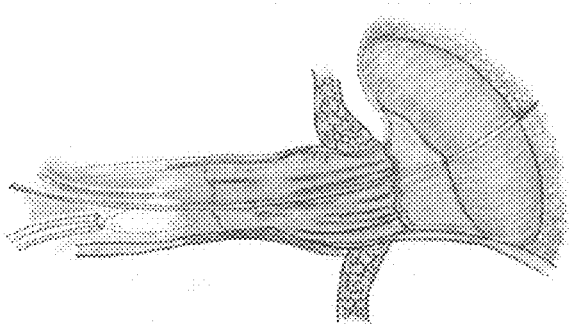
Figure 36A:
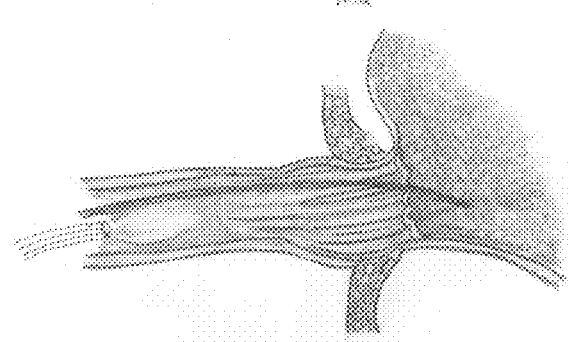

FIG. 36D and FIG. 37D illustrate two alternative treatment options relating to bulking and gathering. In FIG. 36D, the LES is repositioned with bulking material such as a chitosan-dimeric naphthalimide complex or conjugate, as described, for example, in U.S. Pat. No. 7,514,399. Alternatively, in FIG. 37D, the LES is repositioned with suture in a gathering fashion.

In FIGS. 36E and 37E, the size and pressure are determined. Activation is initiated.

FIGS. 36F and 37F show the restored esophageal tone, LES pressure and healing of the damaged tissue.

All patent publications and non-patent publications referenced herein are indicative of the level of skill of those skilled in the art to which this invention pertains. All these publications are herein incorporated by reference to the same extent as if each individual publication were specifically and individually indicated as being incorporated by reference.

At various places in the present specification, values are disclosed in groups or in ranges. It is specifically intended that the description include each and every individual subcombination of the members of such groups and ranges and any combination of the various endpoints of such groups or ranges. For example, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20. Real numbers are intended to be similarly inclusive, including values up to at least three decimal places.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Moreover, while illustrative embodiments have been described herein, the scope of any and all embodiments include equivalent elements, modifications, omissions, combinations (e.g., of aspects across various embodiments), adaptations and/or alterations as would be appreciated by those skilled in the art based on the present disclosure. The limitations in the claims are to be interpreted broadly based on the language employed in the claims and not limited to examples described in the present application. The examples are to be construed as non-exclusive. Furthermore, the steps of the disclosed methods may be modified in any manner, including by reordering steps and/or inserting or deleting steps. It is intended, therefore, that the specification and examples be considered as illustrative only, with a true scope and spirit being indicated by the following claims and their full scope of equivalents.

What is claimed is:

1. A method of inhibiting loss of an increased lumen in an area of stenosis of the digestive system following dilatation of the stenotic area in a subject, comprising administering to an area of the dilatation a composition comprising an effective amount of a dimeric naphthalimide, or a pharmaceutically acceptable salt thereof, and activating the dimeric naphthalimide via electromagnetic energy, wherein the dimeric naphthalimide is represented by any one of structures I, II and III:

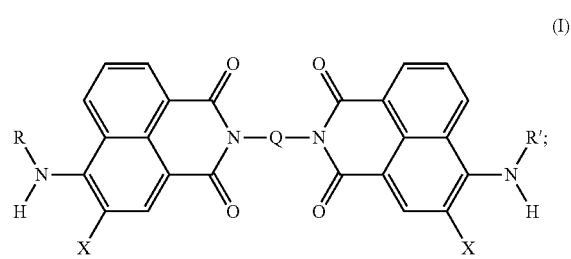

(I)

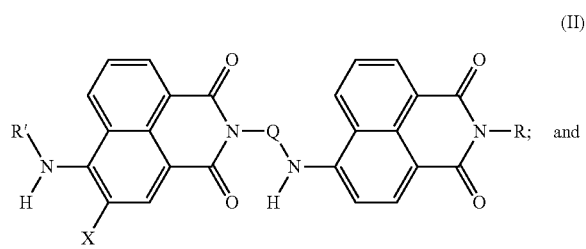

(II)

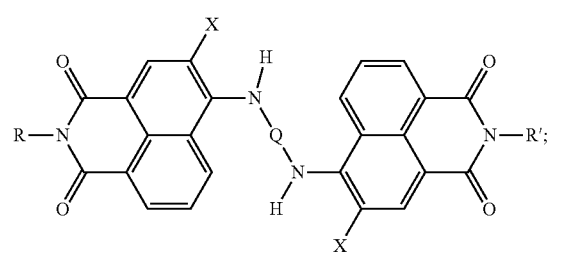

(III)

wherein R, R', and Q are each independently selected from the group consisting of straight-chain and branched chain alkyl groups having from 2 to 50 carbons, optionally substituted with one or more ether groups, one or more amide groups, or one or more amine groups; and wherein X is hydrogen, a halogen, a sulfonate ester or a quaternary ammonium salt.

2. A method of increasing luminal diameter of an area of stenosis of the esophagus of a subject in need thereof, comprising administering to the area a composition comprising an effective amount of a dimeric naphthalimide, or a pharmaceutically acceptable salt thereof, and activating the dimeric naphthalimide via electromagnetic energy, wherein the dimeric naphthalimide is represented by any one of structures I, II and III:

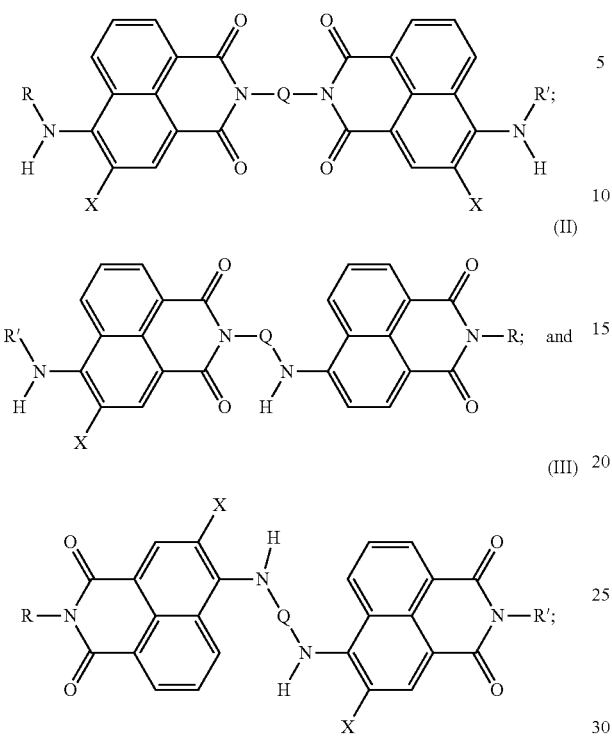

wherein R, R', and Q are each independently selected from the group consisting of straight-chain and branched chain alkyl groups having from 2 to 50 carbons, optionally substituted with one or more ether groups, one or more amide groups, or one or more amine groups; and wherein X is hydrogen, a halogen, a sulfonate ester or a quaternary ammonium salt.

3. A method of restoring tone of the esophagus in a subject in need thereof, comprising administering to an area of the esophagus that exhibits irregular function, an effective amount of a dimeric naphthalimide, or a pharmaceutically acceptable salt thereof, and activating the dimeric naphthalimide via electromagnetic energy, wherein the dimeric naphthalimide is represented by any one of structures I, II and III:

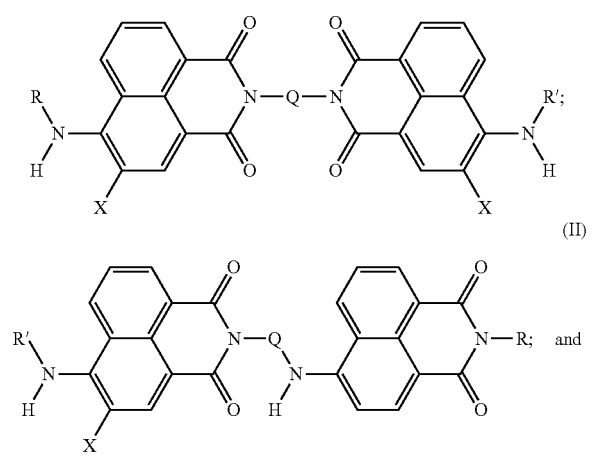

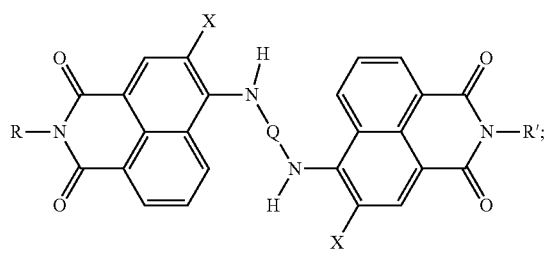

wherein R, R', and Q are each independently selected from the group consisting of straight-chain and branched chain alkyl groups having from 2 to 50 carbons, optionally substituted with one or more ether groups, one or more amide groups, or one or more amine groups; and wherein X is hydrogen, a halogen, a sulfonate ester or a quaternary ammonium salt.

4. A method of enhancing recovery of esophageal tissue following a surgical procedure, comprising administering to a subject at about the time of the surgical procedure, and at the area of the surgical procedure, a composition comprising an effective amount of a dimeric naphthalimide, or a pharmaceutically acceptable salt thereof, and activating the dimeric naphthalimide via electromagnetic energy.

5. The method of claim 1 wherein the dimeric naphthalimide is represented by structure I:

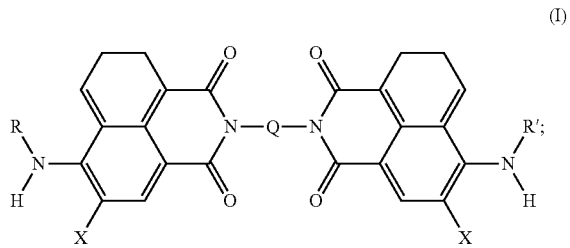

wherein R, R', and Q are each independently selected from the group consisting of straight-chain and branched chain alkyl groups having from 2 to 50 carbons, optionally substituted with one or more ether groups, one or more amide groups, or one or more amine groups; and wherein X is hydrogen, a halogen, a sulfonate ester or a quaternary ammonium salt.

6. The method of claim 1, wherein X is hydrogen.

7. The method of claim 1 wherein Q is a straight-chain or branched chain alkyl group having from 2 to 37 carbons, substituted with one or more ether groups.

8. The method of claim 1 wherein R and R' are each independently selected from the group consisting of straight-chain and branched chain alkyl groups having from 2 to 10 carbons, substituted with one or more ether groups and one or more amide or amine groups.

9. The method of claim 1 wherein the dimeric naphthalimide is represented by structure Ia:

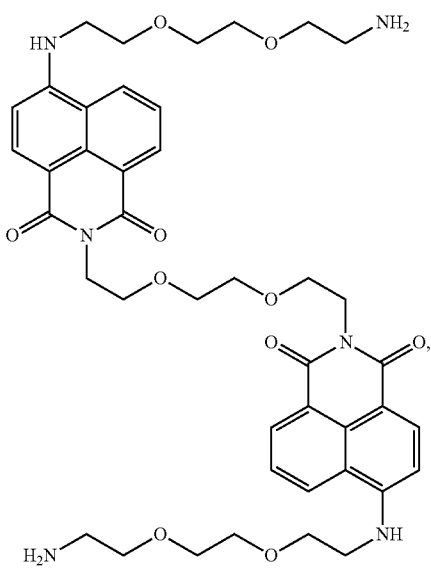

or a pharmaceutically acceptable salt thereof.

10. The method of claim 1 wherein the dimeric naphthalimide is represented by structure IIa:

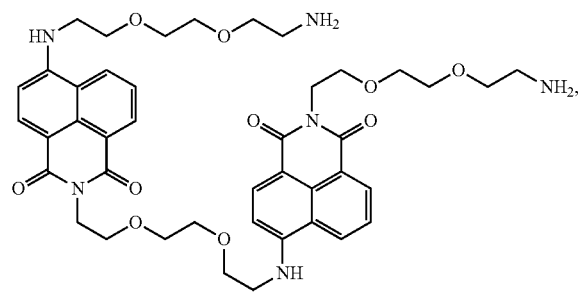

or a pharmaceutically acceptable salt thereof.

11. The method of claim 1 wherein the dimeric naphthalimide is represented by structure IIIa:

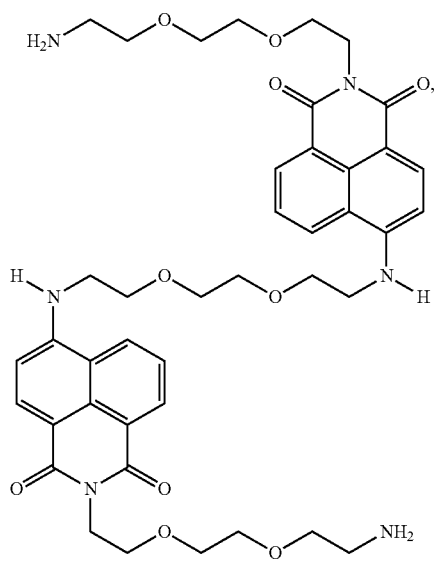

or a pharmaceutically acceptable salt thereof.

12. The method of claim 1 wherein the composition is a liquid and comprises a pharmaceutically acceptable carrier.

13. The method of claim 12, wherein the carrier is aqueous.

14. The method of claim 12, wherein the carrier is non-aqueous.

15. The method of claim 1 wherein the composition further comprises at least one excipient.

16. The method of claim 15, wherein the at least one excipient is selected from antioxidants/free radical scavengers, osmolarity agents, tonicity agents, pH modifiers or modulation agents, surfactants, viscosity agents, penetration enhancers, preservatives, and antiproliferative agents.

17. The method of claim 16, wherein the preservative comprises an C1-C6 alcohol.

18. The method of claim 16, wherein the osmolarity agent comprises a salt.

19. The method of claim 16, wherein the salt is a diacetate or a citrate salt.

20. The method of claim 17 wherein the salt is present in the composition in a concentration of greater than O to about 1 Molar (M).

21. The method of claim 20, wherein the salt is present in the composition in a concentration of about 140 millimolar.

22. The method of claim 12, wherein the liquid composition has a pH ranging from about 2 to about 9.

23. The method of claim 12, wherein the liquid composition has a volume of about 1 to about 20 milliliters (ml).

24. The method of claim 1 wherein the composition is a solid.

25. The method of claim 1 wherein the dimeric naphthalimide or pharmaceutically acceptable salt thereof remains in contact with the area of the dilatation for about 3 to about 7 minutes after the administering.

26. The method of claim 1 wherein the stenosis is in the Gastrointestinal (GI) tract.

27. The method of claim 1 wherein the stenosis is in the esophagus.

28. The method of claim 1 wherein the electromagnetic energy comprises visible light having a wavelength of about 400 to about 500 nm.

29. The method of claim 28, wherein the visible light comprises blue light.

30. The method of claim 29, wherein the blue light has a wavelength of about 440 to about 460 nanometers.

31. The method of claim 1 wherein the activation is conducted for about 1 to about 5 minutes.

32. The method of claim 1 wherein the electromagnetic energy is administered at an intensity of about 30 to about 100 milliwatts (mW)/square centimeter ($cm^2$) of treatment area.

33. The method of claim 1, wherein the dimeric naphthalimide is represented by structure II:

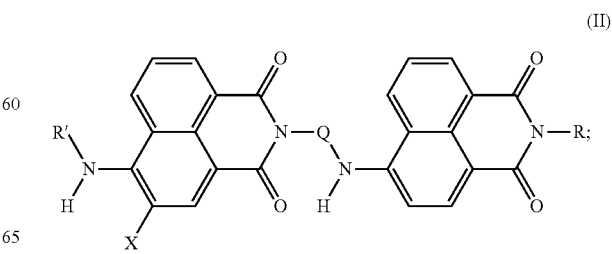

wherein R, R', and Q are each independently selected from the group consisting of straight-chain and branched chain alkyl groups having from 2 to 50 carbons, optionally substituted with one or more ether groups, one or more amide groups, or one or more amine groups; and wherein X is hydrogen, a halogen, a sulfonate ester or a quaternary ammonium salt.

34. The method of claim 1, wherein the dimeric naphthalimide is represented by structure III:

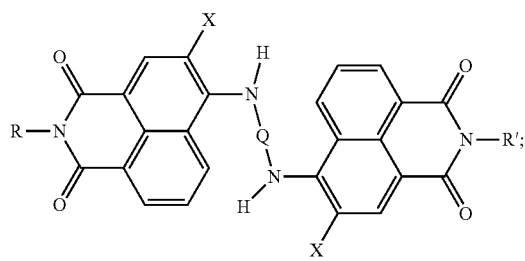

(III)

wherein R, R', and Q are each independently selected from the group consisting of straight-chain and branched chain alkyl groups having from 2 to 50 carbons, optionally substituted with one or more ether groups, one or more amide groups, or one or more amine groups; and wherein X is hydrogen, a halogen, a sulfonate ester or a quaternary ammonium salt.

35. The method of claim 2, wherein the dimeric naphthalimide is represented by structure I:

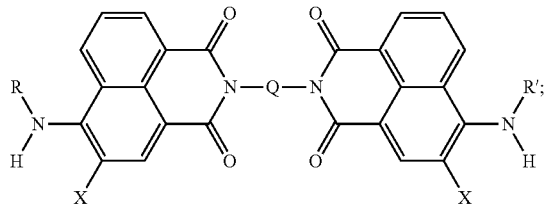

(I)

wherein R, R', and Q are each independently selected from the group consisting of straight-chain and branched chain alkyl groups having from 2 to 50 carbons, optionally substituted with one or more ether groups, one or more amide groups, or one or more amine groups; and wherein X is hydrogen, a halogen, a sulfonate ester or a quaternary ammonium salt.

36. The method of claim 35 wherein the dimeric naphthalimide is represented by structure Ia:

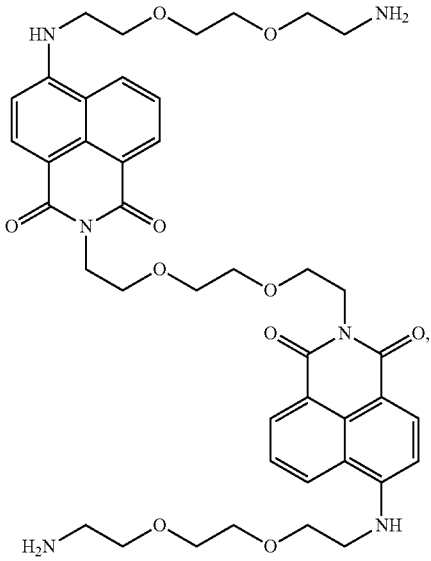

(Ia)

or a pharmaceutically acceptable salt thereof.

37. The method of claim 2, wherein the dimeric naphthalimide is represented by structure II:

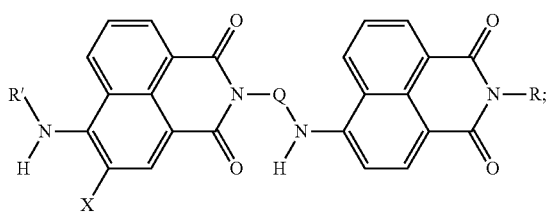

(II)

wherein R, R', and Q are each independently selected from the group consisting of straight-chain and branched chain alkyl groups having from 2 to 50 carbons, optionally substituted with one or more ether groups, one or more amide groups, or one or more amine groups; and wherein X is hydrogen, a halogen, a sulfonate ester or a quaternary ammonium salt.

38. The method of claim 37, wherein the dimeric naphthalimide is represented by structure IIa:

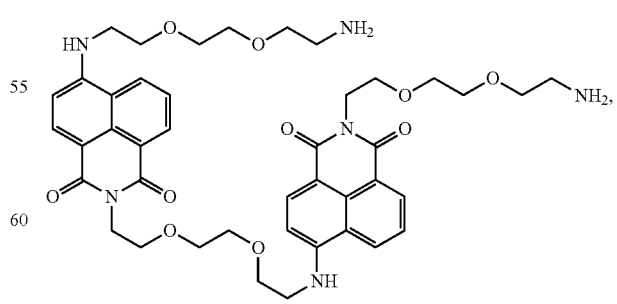

(IIa)

or a pharmaceutically acceptable salt thereof.

39. The method of claim 2, wherein the dimeric naphthalimide is represented by structure III:

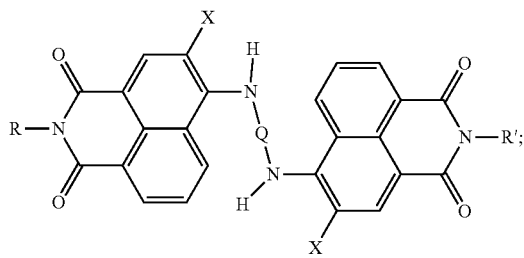

wherein R, R', and Q are each independently selected from the group consisting of straight-chain and branched chain alkyl groups having from 2 to 50 carbons, optionally substituted with one or more ether groups, one or more amide groups, or one or more amine groups; and wherein X is hydrogen, a halogen, a sulfonate ester or a quaternary ammonium salt.

40. The method of claim 39, wherein the dimeric naphthalimide is represented by structure IIIa:

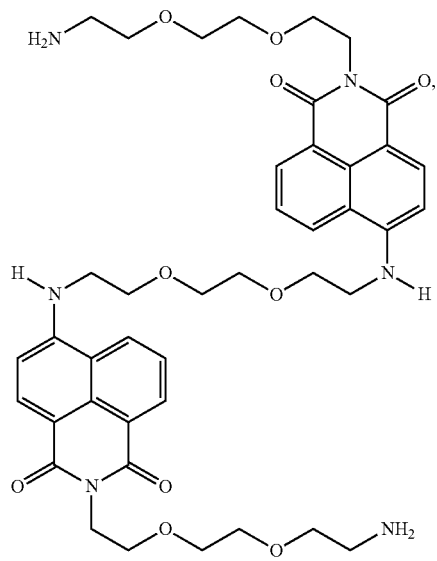

or a pharmaceutically acceptable salt thereof.

41. The method of claim 3, wherein the dimeric naphthalimide is represented by structure I:

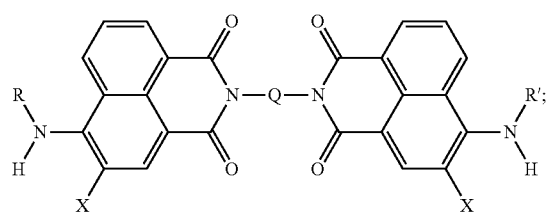

wherein R, R', and Q are each independently selected from the group consisting of straight-chain and branched chain alkyl groups having from 2 to 50 carbons, optionally substituted with one or more ether groups, one or more amide groups, or one or more amine groups; and wherein X is hydrogen, a halogen, a sulfonate ester or a quaternary ammonium salt.

42. The method of claim 41 wherein the dimeric naphthalimide is represented by structure Ia:

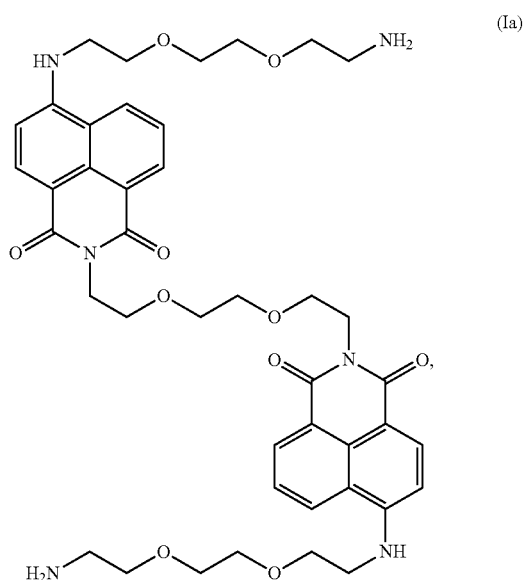

or a pharmaceutically acceptable salt thereof.

43. The method of claim 3, wherein the dimeric naphthalimide is represented by structure II:

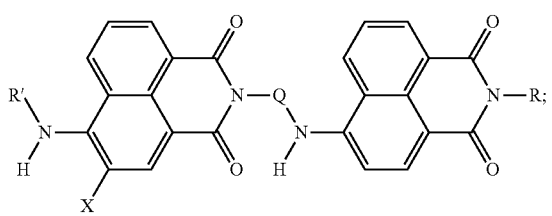

wherein R, R', and Q are each independently selected from the group consisting of straight-chain and branched chain alkyl groups having from 2 to 50 carbons, optionally substituted with one or more ether groups, one or more amide groups, or one or more amine groups; and wherein X is hydrogen, a halogen, a sulfonate ester or a quaternary ammonium salt.

44. The method of claim 43, wherein the dimeric naphthalimide is represented by structure IIa:

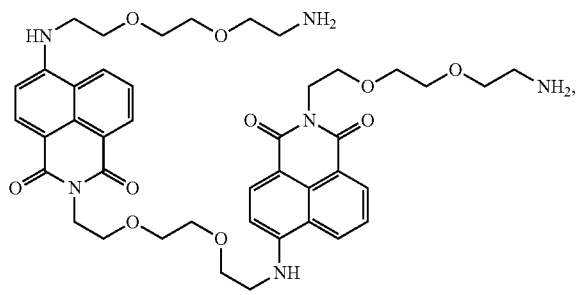

(IIa)

or a pharmaceutically acceptable salt thereof.

45. The method of claim 3, wherein the dimeric naphthalimide is represented by structure III:

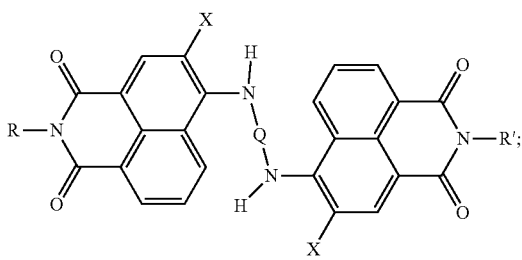

(III)

wherein R, R', and Q are each independently selected from the group consisting of straight-chain and branched chain alkyl groups having from 2 to 50 carbons, optionally substituted with one or more ether groups, one or more amide groups, or one or more amine groups; and wherein X is hydrogen, a halogen, a sulfonate ester or a quaternary ammonium salt.

46. The method of claim 45, wherein the dimeric naphthalimide is represented by structure IIIa:

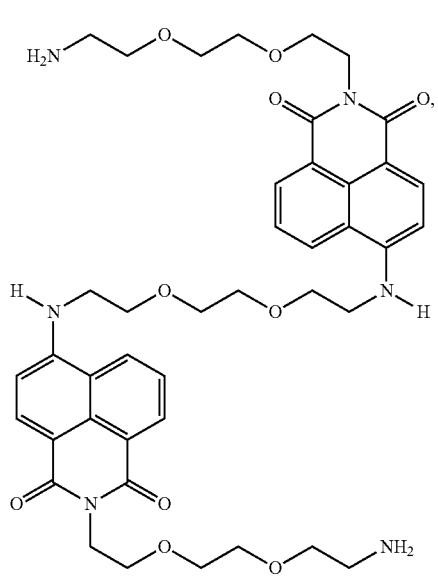

(IIIa)

or a pharmaceutically acceptable salt thereof.

47. The method of claim 4, wherein the dimeric naphthalimide is represented by structure I:

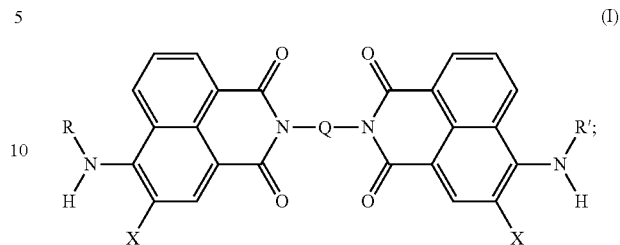

(I)

wherein R, R', and Q are each independently selected from the group consisting of straight-chain and branched chain alkyl groups having from 2 to 50 carbons, optionally substituted with one or more ether groups, one or more amide groups, or one or more amine groups; and wherein X is hydrogen, a halogen, a sulfonate ester or a quaternary ammonium salt.

48. The method of claim 47 wherein the dimeric naphthalimide is represented by structure Ia:

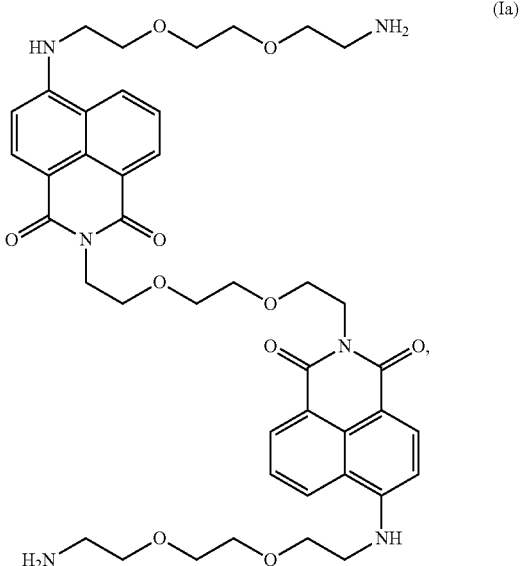

(Ia)

or a pharmaceutically acceptable salt thereof.

49. The method of claim 4, wherein the dimeric naphthalimide is represented by structure II:

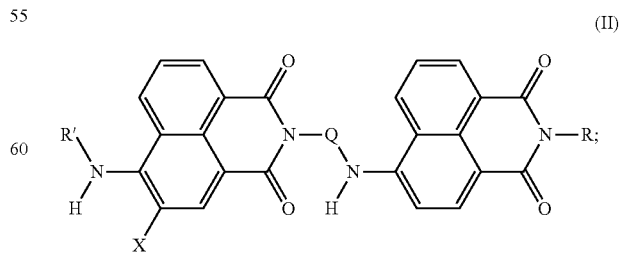

(II)

wherein R, R', and Q are each independently selected from the group consisting of straight-chain and branched chain alkyl groups having from 2 to 50 carbons, optionally substituted with one or more ether groups, one or more amide groups, or one or more amine groups; and wherein X is hydrogen, a halogen, a sulfonate ester or a quaternary ammonium salt.

50. The method of claim 49, wherein the dimeric naphthalimide is represented by structure IIa:

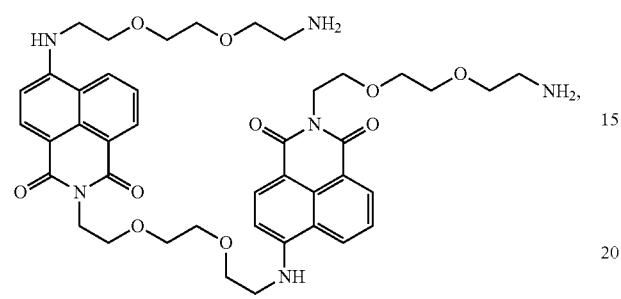

(IIa)

or a pharmaceutically acceptable salt thereof.

51. The method of claim 4, wherein the dimeric naphthalimide is represented by structure III:

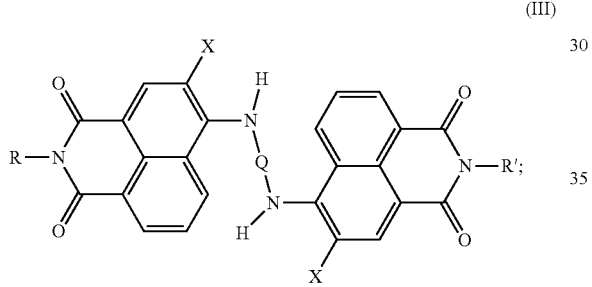

(III)

wherein R, R', and Q are each independently selected from the group consisting of straight-chain and branched chain alkyl groups having from 2 to 50 carbons, optionally substituted with one or more ether groups, one or more amide groups, or one or more amine groups; and wherein X is hydrogen, a halogen, a sulfonate ester or a quaternary ammonium salt.

52. The method of claim 51, wherein the dimeric naphthalimide is represented by structure IIIa:

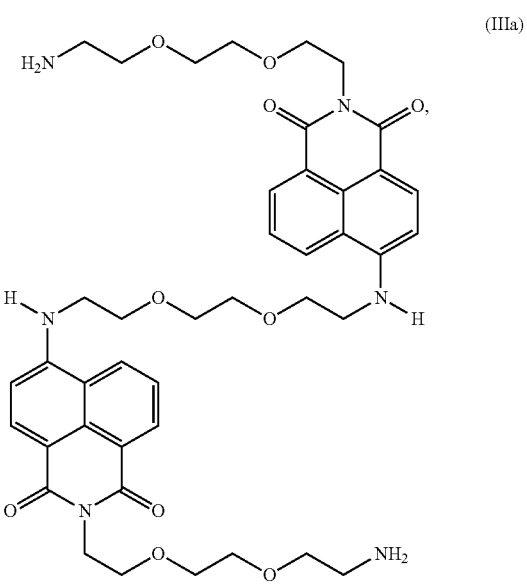 [SMILES: NCCOCCOCCN1C(=O)c2cccc3c(NCCOCCOCCNc4ccc5c6c(cccc46)C(=O)N(CCOCCOCCN)C5=O)ccc(c23)C1=O]

(IIIa)

or a pharmaceutically acceptable salt thereof.

* * * * *